United States Patent
Shaver et al.

(10) Patent No.: US 9,957,216 B2
(45) Date of Patent: May 1, 2018

(54) PROCESSES FOR PRODUCING ACETIC ACID

(71) Applicant: CELANESE INTERNATIONAL CORPORATION, Irving, TX (US)

(72) Inventors: Ronald D. Shaver, Houston, TX (US); Yaw-Hwa Liu, Missouri City, TX (US); Mark O. Scates, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days. days.

(21) Appl. No.: 15/348,338

(22) Filed: Nov. 10, 2016

(65) Prior Publication Data

US 2017/0137361 A1    May 18, 2017

Related U.S. Application Data

(60) Provisional application No. 62/255,049, filed on Nov. 13, 2015.

(51) Int. Cl.
   *C07C 51/12* (2006.01)
   *C07C 51/44* (2006.01)
   *C07C 51/47* (2006.01)

(52) U.S. Cl.
   CPC ............. *C07C 51/12* (2013.01); *C07C 51/44* (2013.01); *C07C 51/445* (2013.01); *C07C 51/47* (2013.01)

(58) Field of Classification Search
   CPC ..................................... C07C 51/12
   USPC ........................................ 562/519
   See application file for complete search history.

(56) References Cited

U.S. PATENT DOCUMENTS

| | | | |
|---|---|---|---|
| 3,769,329 | A | 10/1973 | Paulik et al. |
| 3,772,156 | A | 11/1973 | Johnson et al. |
| 4,302,432 | A | 11/1981 | Polichnowski |
| 4,615,806 | A | 10/1986 | Hilton |

(Continued)

FOREIGN PATENT DOCUMENTS

| | | |
|---|---|---|
| CN | 1349855 | 5/2002 |
| CN | 1640543 | 7/2005 |

(Continued)

OTHER PUBLICATIONS

Title—"Control of propionic acid content in acetic acid production by carbonylation of methanol", Aug. 25, 2013, 20, pp. 50-52, p. 51, right column, line 4-13.

(Continued)

*Primary Examiner* — Deborah D Carr
(74) *Attorney, Agent, or Firm* — Kilpatrick Townsend & Stockton LLP

(57) ABSTRACT

Process for producing acetic acid are disclosed in which a vapor sidedraw is withdrawn from the second column in the primary purification train. The vapor sidedraw comprises acetic acid and lithium-containing compounds at a concentration of no more than 100 wppb. A bottoms stream that is enriched in lithium-containing compounds, such as lithium acetate, or lithium acetate dihydrate, is also withdrawn from the second column. Advantageously, the vapor sidedraw, or a condensed portion thereof, is directly fed to a metal-exchanged ion exchange resin having acid cation exchange sites to produce purified acetic acid. This prevents displacement of the metals in the ion exchange resin.

20 Claims, 1 Drawing Sheet

(56) References Cited

U.S. PATENT DOCUMENTS

| | | |
|---|---|---|
| 4,792,620 A | 12/1988 | Paulik et al. |
| 4,894,477 A | 1/1990 | Scates et al. |
| 4,908,477 A | 3/1990 | Hartmann et al. |
| 5,001,259 A | 3/1991 | Smith et al. |
| 5,026,908 A | 6/1991 | Smith et al. |
| 5,144,068 A | 9/1992 | Smith et al. |
| 5,220,058 A | 6/1993 | Fish et al. |
| 5,344,976 A | 9/1994 | Jones et al. |
| 5,416,237 A | 5/1995 | Aubigne et al. |
| 5,625,095 A | 4/1997 | Miura et al. |
| 5,653,853 A | 8/1997 | Kagotani et al. |
| 5,696,284 A | 12/1997 | Baker et al. |
| 5,731,252 A | 3/1998 | Warner et al. |
| 5,877,347 A | 3/1999 | Ditzel et al. |
| 5,877,348 A | 3/1999 | Ditzel et al. |
| 5,883,295 A | 3/1999 | Sunley et al. |
| 5,932,764 A | 8/1999 | Morris et al. |
| 5,942,460 A | 8/1999 | Garland et al. |
| 5,962,735 A | 10/1999 | Kulprathipanja et al. |
| 6,066,762 A | 5/2000 | Yoneda et al. |
| 6,143,930 A | 11/2000 | Singh et al. |
| 6,225,498 B1 | 5/2001 | Blay et al. |
| 6,303,813 B1 | 10/2001 | Scates et al. |
| 6,323,364 B1 | 11/2001 | Agrawal et al. |
| 6,339,171 B1 | 1/2002 | Singh et al. |
| 6,657,078 B2 | 12/2003 | Scates et al. |
| 7,005,541 B2 | 2/2006 | Cheung et al. |
| 7,342,129 B2 | 3/2008 | Law et al. |
| 7,476,761 B2 | 1/2009 | Kojima |
| 7,678,940 B2 | 3/2010 | Miura et al. |
| 8,168,822 B2 | 5/2012 | Scates |
| 8,940,932 B2 | 1/2015 | Shimizu |
| 8,957,248 B2 | 2/2015 | Miura et al. |
| 9,006,483 B2 | 4/2015 | Shimizu et al. |
| 9,073,843 B2 | 7/2015 | Shimizu et al. |
| 9,115,071 B2 | 8/2015 | Shimizu et al. |
| 2007/0093676 A1* | 4/2007 | Kojima .................. B01J 23/464 562/519 |
| 2009/0187043 A1 | 7/2009 | Scates et al. |
| 2013/0116470 A1 | 5/2013 | Miura et al. |
| 2013/0261334 A1 | 10/2013 | Shimizu et al. |
| 2013/0264186 A1 | 10/2013 | Shimizu et al. |
| 2013/0281735 A1 | 10/2013 | Shimizu et al. |
| 2013/0303800 A1 | 11/2013 | Shumizu |
| 2013/0310603 A1 | 11/2013 | Shimizu et al. |
| 2015/0368176 A1 | 12/2015 | Miura et al. |

FOREIGN PATENT DOCUMENTS

| | | |
|---|---|---|
| CN | 101053841 | 10/2007 |
| CN | 104689854 | 6/2015 |
| EP | 0 161 874 A1 | 11/1985 |
| EP | 0087870 | 9/1987 |
| JP | H8-20555 A | 1/1996 |
| JP | H0867650 A | 3/1996 |
| JP | H10231267 A | 9/1998 |
| JP | 2009-501129 A | 1/2009 |
| WO | 2014/115826 A1 | 7/2014 |

OTHER PUBLICATIONS

Title—"Control of formation of ethanol in methanol", Sep. 15, 2007, $5^{th}$ period, pp. 21-22, left column, lines 8-16.

Title—"A method to reduce ethanol content in purified methanol", Aug. 25, 2010, vol. 33, No. 4, pp. 225-227, p. 225, left column, line 2-9.

Title—"Purification of crude methanol", Jan. 15, 1997, 1997, $1^{st}$ period, pp. 1-5 and 11, p. 2, left column, line 24-right column, line 3.

Kirk-Othmer Encyclopedia of Chemical Technology $4^{th}$ Ed, Mass Transfer to Neuroregulators, A Wiley-Interscience publication; John Wiley & Sons, Inc., vol. 16, 1995, p. 554, lines 9-17.

IMPCA Methanol Reference Specifications, International Methanol Producers & Consumers Association, Dec. 9, 2010, p. 1.

Title: "Specification of ethanol content of methanol products", May 15, 2008, 2008, $3^{rd}$ period, pp. 52-54, p. 53, left column, lines 14-20.

Title: "Consideration for four-column distillation process for methanol production", Sep. 20, 1998, 1998, $9^{th}$ period, pp. 21-22.

Haynes, A. (2010). "Catalytic Methanol Carbonylation," *Advances in Catalysis* 53:1-45.

Haynes, A. (2006, e-pub. May 25, 2006). "Acetic Acid Synthesis by Catalytic Carbonylation of Methanol," in Topics in Organometallic Chemistry, Catalytic Carbonylation Reactions, Springer-Verlag, Berlin, Heidelberg, 18:179-205.

Jones, J.H. (2000). "The Cativa™ Process for the Manufacture of Acetic Acid," Platinum Metals Review 44(3):94-105.

International Search Report receive d in the corresponding PCT Application No. PCT/US2015/053839, dated Jan. 21, 2016, 46 pgs.

International Search Report received in the corresponding International Patent Application No. PCT/US2015/053737, dated Jan. 21, 2016, 11 pgs.

Office Action Cited in U.S. Appl. No. 14/874,332, dated Jan. 6, 2016, 15 pages.

Smith, B.L. et al. (1987). "The Rhodium-Catalyzed Methanol Carbonylation to Acetic Acid at Low Water Concentrations: The Effect of Iodide and Acetate on Catalyst Activity and Stability," Journal of Molecular Catalysis 39:115-136.

Translation of Office Action dated Sep. 18, 2015 in corresponding Japanese Application No. JP2015-115653, 5 pages.

International Search Report and Written Opinion received in the corresponding International Patent Application No. PCT/US2016/061555, dated Feb. 1, 2017.

* cited by examiner

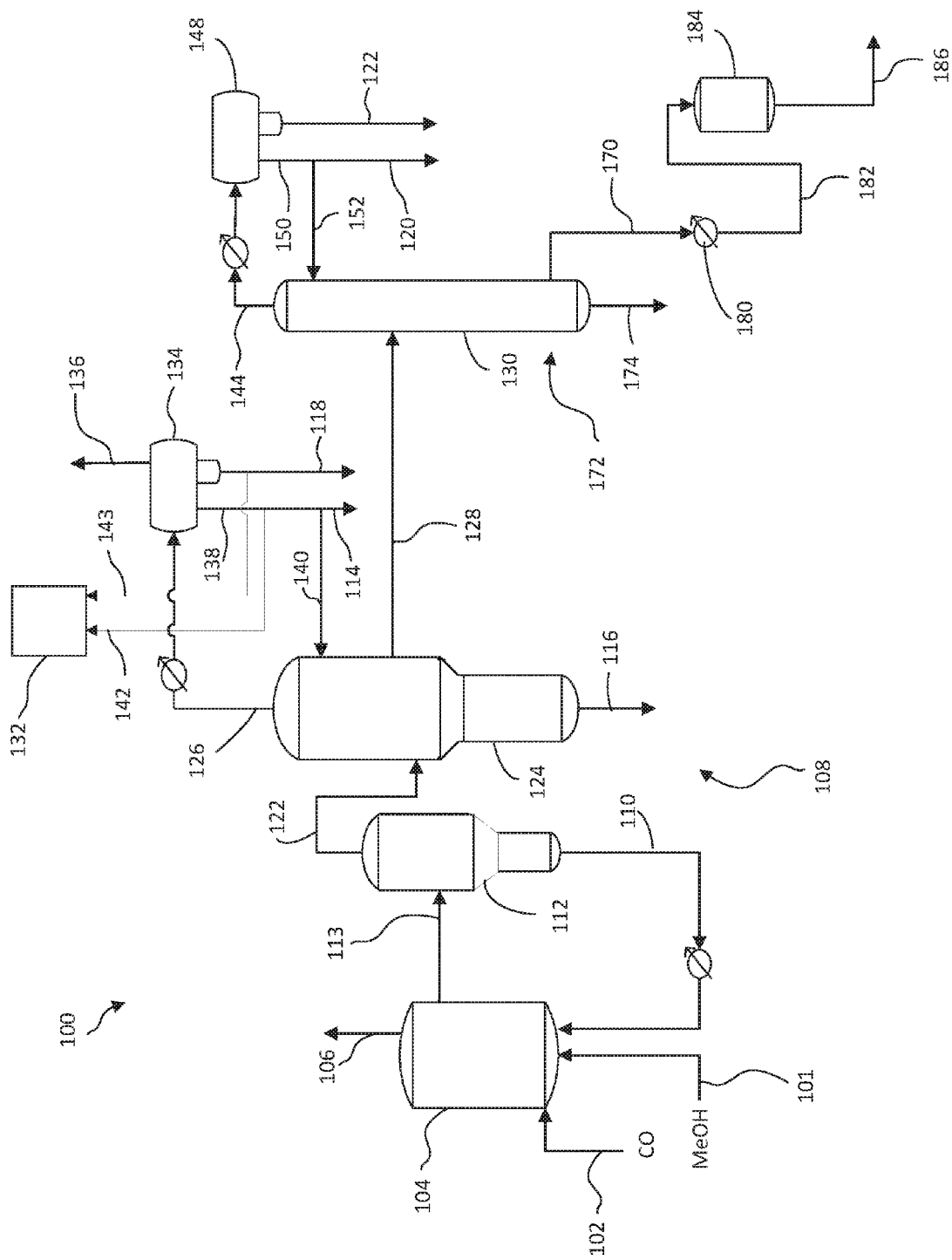

PROCESSES FOR PRODUCING ACETIC ACID

CROSS-REFERENCES TO RELATED APPLICATIONS

This patent application is a continuation-in-part of U.S. patent application Ser. No. 62/255,049, entitled "Processes for Producing Acetic Acid," filed on Nov. 13, 2015, the disclosure of which is incorporated herein by reference in its entirety.

FIELD OF THE INVENTION

This invention relates to processes for producing acetic acid and, in particular, to improved processes for obtaining a vapor sidedraw comprising acetic acid and lithium-containing compounds at a concentration of no more than 100 wppb.

BACKGROUND OF THE INVENTION

Among currently employed processes for synthesizing acetic acid, one of the most useful commercially is the catalyzed carbonylation of methanol with carbon monoxide as taught in U.S. Pat. No. 3,769,329, incorporated herein by reference in its entirety. The carbonylation catalyst contains rhodium, either dissolved or otherwise dispersed in a liquid reaction medium or supported on an inert solid, along with a halogen-containing catalyst promoter as exemplified by methyl iodide. The rhodium can be introduced into the reaction system in any of many forms. Likewise, because the nature of the halide promoter is not generally critical, a large number of suitable promoters, most of which are organic iodides, may be used. Most typically and usefully, the reaction is conducted by continuously bubbling carbon monoxide gas through a liquid reaction medium in which the catalyst is dissolved.

A widely used and successful commercial process for synthesizing acetic acid involves the catalyzed carbonylation of methanol with carbon monoxide. The catalyst contains rhodium and/or iridium and a halogen promoter, typically methyl iodide. The reaction is conducted by continuously bubbling carbon monoxide through a liquid reaction medium in which the catalyst is dissolved. The reaction medium comprises acetic acid, methyl acetate, water, methyl iodide and the catalyst. Commercial processes for the carbonylation of methanol include those described in U.S. Pat. No. 3,769,329, the entireties of which is incorporated herein by reference. Another conventional methanol carbonylation process includes the Cativa™ process, which is discussed in Jones, J. H. (2002), "*The Cativa™ Process for the Manufacture of Acetic Acid*," Platinum Metals Review, 44 (3): 94-105, the entirety of which is incorporated herein by reference.

The AO™ process for the carbonylation of an alcohol to produce the carboxylic acid having one carbon atom more than the alcohol in the presence of a rhodium catalyst is disclosed in U.S. Pat. Nos. 5,001,259; 5,026,908; and 5,144,068; and EP0161874, the entireties of which are incorporated herein by reference. As disclosed therein, acetic acid is produced from methanol in a reaction medium containing methyl acetate (MeAc), methyl halide, especially methyl iodide (MeI), and rhodium present in a catalytically effective concentration. These patents disclose that catalyst stability and the productivity of the carbonylation reactor can be maintained at high levels, even at very low water concentrations, i.e., 4 weight percent or less, (despite the prior practice of maintaining approximately 14-15 wt. % water) by maintaining in the reaction medium, along with a catalytically effective amount of rhodium, at least a finite concentration of water, e.g., 0.1 wt. %, and a specified concentration of iodide ions over and above the iodide ion that is present as hydrogen iodide. This iodide ion is a simple salt, with lithium iodide being preferred. The salt may be formed in situ, for example, by adding lithium acetate, lithium carbonate, lithium hydroxide or other lithium salts of anions compatible with the reaction medium. The patents teach that the concentration of methyl acetate and iodide salts are significant parameters in affecting the rate of carbonylation of methanol to produce acetic acid, especially at low reactor water concentrations. By using relatively high concentrations of the methyl acetate and iodide salt, a high degree of catalyst stability and reactor productivity is achieved even when the liquid reaction medium contains water in finite concentrations as low as 0.1 wt. %. Furthermore, the reaction medium employed improves the stability of the rhodium catalyst, i.e., resistance to catalyst precipitation, especially during the product recovery steps of the process. In these steps, distillation for the purpose of recovering the acetic acid product tends to remove from the catalyst the carbon monoxide, which in the environment maintained in the reaction vessel, is a ligand with stabilizing effect on the rhodium.

U.S. Pat. No. 5,144,068, the entirety of which is incorporated herein by reference, discloses a process for producing acetic acid by reacting methanol with carbon monoxide in a liquid reaction medium containing a rhodium (Rh) catalyst and comprising water, acetic acid, methyl iodide, and methyl acetate, wherein catalyst stability is maintained in the reaction by maintaining in said reaction medium during the course of said reaction 0.1 wt. % to 14 wt. % of water together with (a) an effective amount in the range of 2 wt. % to 20 wt. % of a catalyst stabilizer selected from the group consisting of iodide salts which are soluble in said reaction medium in effective concentration at reaction temperature, (b) 5 wt. % to 20 wt. % of methyl iodide, and (c) 0.5 wt. % to 30 wt. % of methyl acetate. Suitable iodide salts may be a quaternary iodide salt or an iodide salt of a member of the group consisting of the metals of Group IA and Group IIA of the Periodic Table.

Carbonyl impurities, such as acetaldehyde, that are formed during the carbonylation of methanol may react with iodide catalyst promoters to form multi-carbon alkyl iodides, e.g., ethyl iodide, propyl iodide, butyl iodide, pentyl iodide, hexyl iodide, and the like. It is desirable to remove multi-carbon alkyl iodides from the reaction product because even small amounts of these impurities in the acetic acid product tend to poison the catalyst used in the production of vinyl acetate, a product commonly produced from acetic acid.

Conventional techniques to remove such impurities include treating the crude acid product streams with oxidizers, ozone, water, methanol, activated-carbon, amines, and the like. Such treatments may or may not be combined with distillation of the acetic acid. The most typical purification treatment involves a series of distillations to yield a suitable purified acetic acid as the final product. It is also known to remove carbonyl impurities from organic streams by treating the organic streams with an amine compound such as hydroxylamine, which reacts with the carbonyl compounds to form oximes, followed by distillation to separate the purified organic product from the oxime reaction products. However, the additional treatment of the purified acetic acid adds cost to the process, and distillation of the treated acetic acid product can result in additional impurities being formed.

While it is possible to obtain acetic acid of relatively high purity, the acetic acid product formed by the low-water carbonylation process and purification treatment described above frequently remains somewhat deficient with respect to the permanganate time due to the presence of small proportions of residual impurities. Because a sufficient permanganate time is an important commercial test, which the acid product may be required to meet to be suitable for many uses, the presence of impurities that decrease permanganate time is objectionable. Moreover, it has not been economically or commercially feasible to remove minute quantities of these impurities from the acetic acid by distillation because some of the impurities have boiling points close to that of the acetic acid product or halogen-containing catalyst promoters, such as methyl iodide. It has thus become important to identify economically viable methods of removing impurities elsewhere in the carbonylation process without contaminating the purified acetic acid or adding unnecessary costs.

Macroreticulated or macroporous strong acid cationic exchange resin compositions are conventionally utilized to reduce iodide contamination. Suitable exchange resin compositions, e.g., the individual beads thereof, comprise both sites that are functionalized with a metal, e.g., silver, mercury or palladium, and sites that remain in the acid form. Exchange resin compositions that have little or no metal-functionality do not efficiently remove iodides and, as such, are not conventionally used to do so. Typically, metal-functionalized exchange resins are provided in a fixed bed and a stream comprising the crude acetic acid product is passed through the fixed resin bed. In the metal functionalized resin bed, the iodide contaminants contained in the crude acetic acid product are removed from the crude acid product stream.

U.S. Pat. No. 6,657,078 describes a low-water process that uses a metal-functionalized exchange resin to remove iodides. The reference also avoids the use of a heavy ends column, resulting in an energy savings.

The metal-functionalization of exchange resin compositions often involves significant processing and expense, often costing orders of magnitude more than resins that are not metal-functionalized. Often the process steps associated with the functionalization varies very little with regard to the actual amount of metal that is deposited on the exchange resin. For example, the processing necessary to functionalize 50% of the active sites of a quantity of exchange resin is quite similar to the processing necessary to functionalize 10% of the active sites of the same quantity of exchange resin. Because the entire quantity of exchange resin requires processing, however, both the 50%-functionalized exchange resin and the 10%-functionalized resin require significantly more processing than the same quantity of non-functionalized resin.

Other ion exchange resins have been used to remove iodide impurities from acetic acid and/or acetic anhydride. There is disclosed in U.S. Pat. No. 5,220,058 the use of ion exchange resins having metal exchanged thiol functional groups for removing iodide impurities from acetic acid and/or acetic anhydride. Typically, the thiol functionality of the ion exchange resin has been exchanged with silver, palladium, or mercury.

In addition to iodide contaminants, metals from the walls of the vessels used in the acetic acid production system often corrode and dissolve into the crude acetic acid product compositions. Thus, conventional crude acid product streams often comprise corrosion metal contaminants as well as iodide contaminants. These corrosion metals are known to interfere with the carbonylation reaction or accelerate competing reactions such as the water-gas shift reaction. Typically, these corrosion metals may be removed from the process streams by passing the streams through resin beds comprising standard macroreticular or macroporous cationic exchange resins.

In a case where a silver, mercury or palladium exchanged resin is utilized, however, the soluble corrosion metal cations may detrimentally displace the metal-functionalized sites of the exchange resins. As such, these exchange sites are unable to capture/remove the iodide contaminants. The lifetime of the functionalized resin, with regard to iodide removal, is shortened by the presence of corrosion metals. Often a pre-determined portion of the sites of the exchange resin composition are functionalized, thus leaving the remainder of the sites in the acid form. As a result, the acid sites capture much of the corrosion metals while many of the functionalized sites remain available for iodide removal. Although this technique may improve the lifetime of exchange resins, the partial functionalization of the pre-determined portion of sites requires significant processing and resources.

In addition, it has been found that a problem associated with the use of silver-exchanged strong acid cation exchange resins is that the silver may actually be displaced by corrosion metals, as described in U.S. Pat. No. 5,344,976. According to this patent, the metal ion contaminants in the acid and/or anhydride may arise from corrosion or the use of reagents in the up stream process. The patent describes the use of a cationic exchanger in the acid form to remove at least a portion of the metal ion contaminants such as iron, potassium, calcium, magnesium, and sodium from a carboxylic acid stream prior to contacting the stream with the exchanged strong acid cation exchange resin to remove $C_1$ to $C_{10}$ alkyl iodide compounds, hydrogen iodide or iodide salts.

In addition, other schemes introduce other contaminants that may need to be removed from the product. For example, it has been well known in the art for some time that adding an alkali component, such as KOH, to the drying column of a carbonylation purification process is useful to inhibit the buildup of HI in the column as described in U.S. Pub. No. 2013/0264186, U.S. Pat. No. 3,772,156, and U.S. Pat. No. 7,678,940.

U.S. Pub. No. 2015/0368176 discloses treating the carboxylic acid-containing stream obtained from the second flash system or the adsorption system with an ion exchange resin that allows for the production of high-purity carboxylic acid product from which halides such as iodides (e.g., alkyl iodides) have been removed to a high degree.

U.S. Pat. No. 7,678,940 discloses a process for producing a purified carboxylic acid having "n+1" carbon atoms comprises feeding a carboxylic acid stream containing a carboxylic acid having "n+1" carbon atoms, a hydrogen halide, a lower boiling point (bp) component, a higher bp component, and others to a first distillation column; separating a lower bp fraction containing part of the lower bp component and a higher bp fraction containing part of the higher bp component in the first column; withdrawing a side stream containing at least the carboxylic acid by side cut from the first column; feeding the side stream to a second distillation column; separating a lower bp fraction containing part of the lower bp component and a higher bp fraction containing part of the higher bp component in the second column; and withdrawing a side stream containing the carboxylic acid by side cut from the second column to recover a purified carboxylic acid; and the process further comprises feeding at least one first component (A) selected from the group consisting of an alcohol, corresponding to the carboxylic acid, having "n" carbon atom(s), and an ester of the alcohol with the carboxylic acid to the first column, and if necessary, water.

Other processes remove corrosion metal contaminants at different stages of the process, for example from the reactant composition. U.S. Pat. No. 4,894,477 describes a process that uses strongly acidic ion exchange resins in the lithium form to remove corrosion metal contaminants. U.S. Pat. No. 5,731,252 describes contacting the catalyst solution with an ion exchange resin bed, in the lithium form, while requiring simultaneous addition of a sufficient amount of water to allow the corrosion metal salts in the catalyst medium to dissociate so that ion exchange can occur and the corrosion metals can be removed from the reactor catalyst solution.

While the above-described processes have been successful, the need exists for process for improved processes for producing acetic acid, in particular, low water and low energy processes and methods for removing contaminants from those processes.

SUMMARY OF THE INVENTION

This invention relates to processes for the production of acetic acid. In one embodiment the present invention relates a process for producing acetic acid comprising carbonylating at least one member selected from the group consisting of methanol, dimethyl ether, and methyl acetate in a reaction medium comprising a rhodium catalyst, water, methyl iodide and lithium-containing compounds comprising lithium iodide, lithium hydroxide, lithium acetate, lithium acetate dihydrate, lithium carbonate, lithium alkyl carbonate, methyllithium, lithium chloride, lithium oxalate or mixtures thereof. In one embodiment, the reaction medium may also comprise methyl acetate and/or iodide salts, such as lithium iodide. The process further comprises separating the reaction medium into a liquid recycle stream and a vapor product stream comprising acetic acid, distilling the vapor product stream in a first column to form an overhead comprising water and methyl iodide and a crude product stream comprising acetic acid, distilling the crude product stream in a second column to form a vapor sidedraw comprising acetic acid and lithium-containing compounds at a concentration of no more than 100 wppb, e.g., no more than 50 wppb, and a bottoms stream enriched in lithium-containing compounds, and feeding the vapor sidedraw to a metal-exchanged ion exchange resin having acid cation exchange sites to produce purified acetic acid. The vapor sidedraw or a condensed portion thereof, may be directly fed to the metal-exchanged ion exchange resin. In one embodiment, the bottoms stream comprises lithium-containing compounds at a concentration of greater than 100 wppb, and more preferably no more than 10 wppm. The bottoms stream further comprises rhodium and/or a carbonyl-group containing impurity having a boiling point higher than acetic acid. The bottoms stream may comprise rhodium in an concentration of greater than or equal to 100 wppb. The bottoms stream may comprise the carbonyl group-containing impurity having a boiling point higher than acetic acid in an concentration of greater than or equal to 10 wt. %. The bottoms stream further comprises acetic acid in an concentration of no more than 90 wt. % and water in an concentration of no more than 0.1 wt. %. Other impurities may include iron at a concentration of no more than 1.5 wppm, chloride at a concentration of no more than 0.5 wppm, and/or formic acid at a concentration of no more than 0.01 wppm. In some embodiments, the process also comprises recovering acetic acid from the bottoms stream. In another embodiment, the vapor sidedraw comprises the lithium-containing compounds at a concentration from 1 to 100 wppb and acetic acid in an concentration of greater than or equal to 99.5 wt. %. The vapor sidedraw also may comprise water in an concentration of no more than 0.2 wt. %, e.g., no more than 0.15 wt. %. In one embodiment, the purified acetic acid has a displaced metal concentration of no more than 2000 wppb, wherein the displaced metal is selected from the group consisting of silver and mercury. The purified acetic acid may comprise iodides at a concentration of no more than 100 wppb. The vapor sidedraw may be withdrawn at a point within 5 actual stages from the base of the second column. The first or the second column has an inner pressure from 0.01 to 0.7 MPa and the temperature in the first column is about 50 to 150° C. In one embodiment, the metal-exchanged ion exchange resin has a proportion of the active sites exchanged to metal from 10 to 80% by mol. The process may further comprise measuring the concentration of lithium-containing compounds in the vapor sidedraw.

In another embodiment the present invention relates to a process for producing acetic acid comprising carbonylating at least one member selected from the group consisting of methanol, dimethyl ether, and methyl acetate in a reaction medium comprising a rhodium catalyst, water, methyl iodide and lithium-containing compounds, separating the reaction medium into a liquid recycle stream and a vapor product stream comprising acetic acid, distilling the vapor product stream in a first column to form an overhead and a crude product stream comprising acetic acid, distilling the crude product stream in a second column to form a vapor sidedraw comprising acetic acid and lithium-containing compounds at a concentration of no more than 100 wppb, and a bottoms stream enriched in lithium-containing compounds, condensing the vapor sidedraw to form a condensed sidedraw, and feeding the condensed sidedraw to a metal-exchanged ion exchange resin having acid cation exchange sites to produce purified acetic acid. The condensed sidedraw has a temperature of greater than 25° C., and is within the range from 25 to 125° C. The rate of the condensed sidedraw to be passed through the metal exchanged ion exchange resin is about 3 to 40 bed volumes per hour. The vapor sidedraw may be withdrawn at a point within 5 actual stages from the base of the second column. The condensed portion thereof, may be directly fed to the metal-exchanged ion exchange resin. In one embodiment, the bottoms stream comprises lithium-containing compounds at a concentration of greater than 100 wppb, and more preferably no more than 10 wppm. The bottoms stream further comprises rhodium and a carbonyl-group containing impurity having a boiling point higher than acetic acid. The bottoms stream may comprise rhodium in an concentration of greater than or equal to 100 wppb. The bottoms stream may comprise the carbonyl-group containing impurity having a boiling point higher than acetic acid in an concentration of greater than or equal to 10 wt. %. The bottoms stream further comprises acetic acid in an concentration of no more than 90 wt. % and water in an concentration of no more than 0.1 wt. %. Other impurities may include, iron at a concentration of no more than 1.5 wppm, chloride at a concentration of no more than 0.5 wppm, and/or formic acid at a concentration of no more than 0.01 wppm. In some embodiments, the process also comprises recovering acetic acid from the bottoms stream. In another embodiment, the condensed sidedraw comprises the lithium-containing compounds at a concentration from 1 to 100 wppb and acetic acid in an concentration of greater than or equal to 99.5 wt. %. The condensed sidedraw also may comprise water in an concentration of no more than 0.2 wt. %, e.g., no more than 0.15 wt. %. In one embodiment, the purified acetic acid has a displaced metal concentration of no more than 2000 wppb, wherein the displaced metals are selected from the group consisting of silver and mercury. The purified acetic acid may comprise iodides at a concentration of no more than 100 wppb. The first or the second column has an inner pressure from 0.01 to 0.7 MPa and the temperature in the first column is about 50 to 150° C. In one embodiment, the metal-exchanged ion exchange resin has a proportion of the active sites exchanged to metal from 10 to 80% by mol. The process may further comprise measuring the concentration of lithium-containing compounds in the condensed sidedraw.

BRIEF DESCRIPTION OF THE DRAWINGS

The present invention will be better understood in view of the appended non-limiting FIGURES, wherein:

FIG. 1 illustrates a process for producing acetic acid having a vapor sidedraw in a second column.

DETAILED DESCRIPTION OF THE INVENTION

At the outset, it should be noted that in the development of any such actual embodiment, numerous implementation—specific decisions must be made to achieve the developer's specific goals, such as compliance with system related and business related constraints, which will vary from one implementation to another. In addition, the processes disclosed herein can also comprise components other than those cited or specifically referred to, as is apparent to one having average or reasonable skill in the art.

In the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, a range "from 1 to 10" is to be read as indicating each and every possible number along the continuum between about 1 and about 10. Thus, even if specific data points within the range, or even no data points within the range, are explicitly identified or refer to only a few specific data points, it is to be understood that inventors appreciate and understand that any and all data points within the range are to be considered to have been specified, and that inventors possessed knowledge of the entire range and all points within the range.

Throughout the entire specification, including the claims, the following terms have the indicated meanings unless otherwise specified.

As used in the specification and claims, "near" is inclusive of "at." The term "and/or" refers to both the inclusive "and" case and the exclusive "or" case, and is used herein for brevity. For example, a mixture comprising acetic acid and/or methyl acetate may comprise acetic acid alone, methyl acetate alone, or both acetic acid and methyl acetate.

All percentages are expressed as weight percent (wt. %), based on the total weight of the particular stream or composition present, unless otherwise noted. Room temperature is 25° C. and atmospheric pressure is 101.325 kPa unless otherwise noted.

For purposes herein: acetic acid may be abbreviated as "AcOH"; acetaldehyde may be abbreviated as "AcH"; methyl acetate may be abbreviated "MeAc"; methanol may be abbreviated "MeOH"; methyl iodide may be abbreviated as "MeI"; hydrogen iodide may be abbreviated as "HI"; carbon monoxide may be abbreviated "CO"; and dimethyl ether may be abbreviated "DME".

HI refers to either molecular hydrogen iodide or dissociated hydriodic acid when at least partially ionized in a polar medium, typically a medium comprising at least some water. Unless otherwise specified, the two are referred to interchangeably. Unless otherwise specified, HI concentration is determined via acid-base titration using a potentiometric end point. In particular, HI concentration is determined via titration with a standard lithium acetate solution to a potentiometric end point. It is to be understood that for purposes herein, the concentration of HI is not determined by subtracting a concentration of iodide assumed to be associated with a measurement of corrosion metals or other non H+ cations from the total ionic iodide present in a sample.

It is to be understood that HI concentration does not refer to iodide ion concentration. HI concentration specifically refers to HI concentration as determined via potentiometric titration.

This subtraction method is an unreliable and imprecise method to determine relatively lower HI concentrations (i.e., less than about 5 weight percent) due to the fact that it assumes all non-H+ cations (such as cations of Fe, Ni, Cr, Mo) are associated with iodide anion exclusively. In reality, a significant portion of the metal cations in this process can be associated with acetate anion. Additionally, many of these metal cations have multiple valence states, which adds even more unreliability to the assumption on the amount of iodide anion which could be associated with these metals. Ultimately, this method gives rise to an unreliable determination of the actual HI concentration, especially in view of the ability to perform a simple titration directly representative of the HI concentration.

For purposes herein, an "overhead" or "distillate" of a distillation column refers to at least one of the lower boiling condensable fractions which exits at or near the top, (e.g., proximate to the top), of the distillation column, and/or the condensed form of that stream or composition. Obviously, all fractions are ultimately condensable, yet for purposes herein, a condensable fraction is condensable under the conditions present in the process as readily understood by one of skill in the art. Examples of noncondensable fractions may include nitrogen, hydrogen, and the like. Likewise, an overhead stream may be taken just below the upper most exit of a distillation column, for example, wherein the lowest boiling fraction is a non-condensable stream or represents a de-minimis stream, as would be readily understood by one of reasonable skill in the art.

The "bottoms" or "residuum" of a distillation column refers to one or more of the highest boiling fractions which exit at or near the bottom of the distillation column, also referred to herein as flowing from the bottom sump of the column. It is to be understood that a residuum may be taken from just above the very bottom exit of a distillation column, for example, wherein the very bottom fraction produced by the column is a salt, an unusable tar, a solid waste product, or a de-minimis stream as would be readily understood by one of reasonable skill in the art.

For purposes herein, distillation columns comprise a distillation zone and a bottom sump zone. The distillation zone includes everything above the bottom sump zone, i.e., between the bottom sump zone and the top of the column. For purposes herein, the bottom sump zone refers to the lower portion of the distillation column in which a liquid reservoir of the higher boiling components is present (e.g., the bottom of a distillation column) from which the bottom or residuum stream flows upon exiting the column. The bottom sump zone may include reboilers, control equipment, and the like.

It is to be understood that the term "passages", "flow paths", "flow conduits", and the like in relation to internal components of a distillation column are used interchangeably to refer to holes, tubes, channels, slits, drains, and the like, which are disposed through and/or which provide a path for liquid and/or vapor to move from one side of the internal component to the other side of the internal component. Examples of passages disposed through a structure such as a liquid distributor of a distillation column include drain holes, drain tubes, drain slits, and the like, which allow a liquid to flow through the structure from one side to another.

Average residence time is defined as the sum total of all liquid volume hold-up for a given phase within a distillation zone divided by the average flow rate of that phase through the distillation zone. The hold-up volume for a given phase can include liquid volume contained in the various internal components of the column including collectors, distributors and the like, as well as liquid contained on trays, within downcomers, and/or within structured or random packed bed sections.

Vapor Sidedraw

This invention relates to processes for the production of acetic acid and, in particular, to improved processes for obtaining a vapor sidedraw comprising acetic acid and lithium-containing compounds at a concentration of no more than 100 wppb (weight part per billion) from a carbonylation process. In one embodiment, the vapor sidedraw is obtained from a second column in a primary purification train. The primary purification train is directed at removing bulk components, such as water, methyl acetate, methyl iodide, and hydrogen iodide, from the vapor product stream from the reactor/flash vessel to obtain acetic acid. This primary purification train receives the majority of the vapor flow from the reactor and obtains acetic acid as a purified acetic acid. For example, the columns of the primary purification train include the light ends column (first column) and drying column (second column). This primary purification train may exclude columns whose main function is to remove minor components such as acetaldehyde, alkanes, and propionic acid. Low water and low energy processes for producing acetic acid by the carbonylation of methanol have been developed which involve a rhodium-catalyzed system operating at a water concentration of no more than 14 wt. %, and more preferably no more than 4.1 wt. %, and utilizing up to 2 distillation columns in the primary purification train.

The carbonylation reaction process may use cations, such as a lithium cations, as catalyst promoter and these lithium-containing compounds have been found by the inventors of the present application to concentrate in the lower portion of the second column. When acetic acid is removed from the base of the second column, the lithium-containing compounds undesirably build up in the withdrawn stream. To achieve commercially useful acetic acid, the withdrawn stream is contacted with a metal-exchanged strong acid ion exchange resin to remove residual iodides. It has been found that the silver or mercury in the metal-exchanged strong acid ion exchange resin may be displaced by the residual lithium-containing compounds, resulting in lower resin capacity and efficiency and the potential for contaminating the acetic acid with silver or mercury. In one embodiment, the concentration of lithium-containing compounds is reduced by withdrawing a vapor sidedraw from the second column.

In one embodiment, there is provided a process for producing acetic acid comprising carbonylating at least one member selected from the group consisting of methanol, dimethyl ether, and methyl acetate in a reaction medium comprising a rhodium catalyst, water, methyl iodide and lithium-containing compounds, separating the reaction medium into a liquid recycle stream and a vapor product stream comprising acetic acid, distilling the vapor product stream in a first column to form an overhead comprising water and methyl iodide and a crude product stream comprising acetic acid, distilling the crude product stream in a second column to form a vapor sidedraw comprising acetic acid and lithium-containing compounds at a concentration of no more than 100 wppb, and a bottoms stream enriched in lithium-containing compounds, and feeding the vapor sidedraw, preferably a condensed portion of the vapor sidedraw, to a metal-exchanged ion exchange resin having acid cation exchange sites to produce purified acetic acid.

The vapor sidedraw is withdrawn within 5 actual stages of the base, e.g., within 4 actual stages, within 3 actual stages, within 2 actual stages, within 1 actual stage, and preferably above the base of the second column. An actual stage may correspond to a plate in a column. By withdrawing the vapor sidedraw at such a location the concentration of lithium-containing compounds may be maintained in an acceptable level that does not result in displacement of the metals in the metal-exchanged strong acid ion exchange resin. The lithium-containing compounds concentrated in the lower portion of the second column are removed in a bottoms stream withdrawn from the base, which is enriched in lithium-containing compounds as compared to the vapor sidedraw.

By maintaining low concentrations of lithium-containing compounds in the vapor sidedraw, a separate removal of lithium-containing compounds is advantageously eliminated. In one embodiment, the vapor sidedraw may be condensed and directly fed to the metal-exchanged ion exchange resin having acid cation exchange sites to produce purified acetic acid, without a separate processing step to remove lithium-containing compounds.

The vapor sidedraw is enriched in acetic acid. In one embodiment, vapor sidedraw comprises acetic acid at a concentration of greater than or equal to 99.5 wt. %, e.g., greater than or equal to 99.7 wt. % or greater than or equal to 99.9 wt. %. In addition, the primary component of acetic acid, the vapor sidedraw may also comprise lithium-containing compounds of no more than 100 wppb, e.g., no more than 90 wppb, no more than 80 wppb, no more than 70 wppb, no more than 60 wppb, no more than 50 wppb, no more than 40 wppb, no more than 20 wppb, or no more than 0 wppb. In some embodiments, the vapor sidedraw may comprises no lithium-containing compounds. Thus, in terms of ranges, the vapor sidedraw has a concentration of lithium-containing compounds from 0 to 100 wppb, e.g., from 1 to 100 wppb, from 1 to 90 wppb, from 1 to 80 wppb, from 1 to 70 wppb, from 1 to 60 wppb, from 1 to 50 wppb, from 1 to 40 wppb, from 1 to 30 wppb, from 1 to 20 wppb, or from 1 to 10 wppb. Even very small amounts of lithium, e.g., 10 wppb, present in the crude acid product may cause problem for removing iodides using an metal-exchanged ion exchange resin and/or displacement of metals from the metal-exchanged ion exchange resin. Reducing the concentration of lithium-containing compounds may greatly extend the life of the metal-exchanged resin.

Lithium-containing compounds may include compounds such as lithium iodide, lithium hydroxide, lithium acetate, lithium acetate dihydrate, lithium carbonate, lithium alkyl carbonate, methyllithium, lithium chloride, or lithium oxalate. Other lithium cations may also be present in the lower portion of the second column and may also be present in the vapor sidedraw. In one preferred embodiment, the lithium-containing compounds are lithium acetate and/or lithium acetate dehydrate, and the vapor sidedraw comprises lithium acetate and/or lithium acetate dihydrate at a concentration of no more than 100 wppb, e.g., no more than 90 wppb, no more than 80 wppb, no more than 70 wppb, no more than 60 wppb, no more than 50 wppb, no more than 40 wppb, no more than 20 wppb, or no more than 0 wppb. Thus, in one embodiment, vapor sidedraw may comprise acetic acid at a concentration of greater than or equal to 99.5 wt. %, and lithium acetate and/or lithium acetate dihydrate at a concentration of no more than 100 wppb.

The bottoms stream obtained from the base of the second column is enriched in lithium-containing compounds as compared to the vapor sidedraw. In one embodiment, the bottoms stream comprises acetic acid at a concentration of no more than 90 wt. %, e.g., no more than 85 wt. %, no more than 80 wt. %, or no more than 50 wt. %. Lithium-containing compounds are enriched in the bottoms stream and, in one embodiment, the bottoms stream comprises lithium-containing compounds at a concentration of no more than 100 wppm (weight part per million), e.g., no more than 90 wppm, no more than 80 wppm, no more than 70 wppm, no more than 60 wppm, no more than 50 wppm, or no more than 40 wppm, and/or the bottoms stream comprises lithium-containing compounds at a concentration of greater than 0.5 wppm, e.g., greater than 1 wppm, greater than 5 wppm, greater than 10 wppm, or greater than 20 wppm. In one embodiment, the concentration of lithium-containing compounds in the bottoms stream is greater than the concentration of the lithium-containing compounds in the vapor sidedraw. For example, in one embodiment, when the vapor sidedraw contains 50 wppb, the bottoms stream may comprise lithium-containing compounds at a concentration of greater than 0.5 wppm. In one embodiment, there is provided a process for producing acetic acid comprising carbonylating at least one member selected from the group consisting of methanol, dimethyl ether, and methyl acetate in a reaction medium comprising a rhodium catalyst, water, methyl iodide and lithium-containing compounds, separating the reaction medium into a liquid recycle stream and a vapor product stream comprising acetic acid, distilling the vapor product stream in a first column to form an overhead comprising water and methyl iodide and a crude product stream comprising acetic acid, distilling the crude product stream in a second column to form a vapor sidedraw comprising acetic acid and a bottoms stream comprising acetic acid at a concentration of no more than 90 wt. % and, wherein the concentration of lithium-containing compounds in the bottoms stream is greater than the concentration of the lithium-containing compounds in the vapor sidedraw, and feeding the vapor sidedraw, preferably a condensed portion of the vapor sidedraw, to a metal-exchanged ion exchange resin having acid cation exchange sites to produce purified acetic acid.

It should be understood that because the vapor sidedraw contains the acetic acid for the product, the relative flow rate of the vapor sidedraw is larger than the relative flow rate bottoms stream. The relative flow rate may be determined by the percent of flow rate of the stream compared to the feed to the column. In one embodiment, the relative flow of the vapor sidedraw is at least 5× larger than the relative flow of the bottoms stream, e.g., at least 7× larger, at least 10× larger, at least 12× larger, at least 15× larger, or at least 20× larger. In one exemplary embodiment, the flow rate of the feed to the column 100, the relative flow rate of the vapor sidedraw is from 90% to 99%, while the relative flow rate of the bottoms stream is less than 10%. Thus, in this exemplary embodiment, the relative flow rate of the vapor sidedraw is at least 9× larger than the bottoms stream.

According to the processes disclosed herein, water is removed in the second column and thus the water concentrations in both the vapor sidedraw and bottoms stream are low. In one embodiment, vapor sidedraw comprises water at a concentration of no more than 0.2 wt. %, e.g., no more than 0.15 wt. %, no more than 0.1 wt. %, or no more than 0.05 wt. %. The location of the vapor sidedraw may be chosen to maintain water in the vapor sidedraw at these low concentrations. Maintaining low concentrations of the water in the vapor sidedraw may also contribute to reducing the methyl acetate and methyl iodide concentrations and result in a commercially useful acetic acid. Withdrawing the vapor sidedraw at a higher location in the second column may result in increased water concentrations which are disadvantageous to produce glacial acetic acid. In general by maintaining low water concentration in the vapor sidedraw the water concentrations of the bottoms stream may also be low. In one embodiment, bottoms stream comprises water in concentration of no more than 0.1 wt. %, e.g., no more than 0.05 wt. %, no more than 0.01 wt. %, or no more than 0.005 wt. %.

In one embodiment, vapor sidedraw after being removed from second column is condensed and directly fed to the metal-exchanged ion exchange resin to produce purified acetic acid. It should be understood that the vapor sidedraw and the condensed portion thereof have same compositions and percentage in terms of acetic acid, lithium-containing compounds, and water, as well as other impurities disclosed herein.

Source of Lithium

Unlike other metals that may be present in the product stream that are the result of corrosion metals or metals from the upstream process, i.e. adding after the reactor, lithium cations may be derived from and/or generated by the lithium compound in the reaction medium. It was previously understood that the lithium-containing compounds were less volatile and remained in the liquid recycle from the flash vessel. It has now been discovered that lithium-containing compounds derived from and/or generated by the lithium compound in the reaction medium may be entrained or be volatile enough to concentrate with the product stream after purification in the primary purification trains. The lithium-containing compounds may be difficult to remove. In the metal-exchange guard bed to remove iodide, the lithium-containing compounds may adversely replace metals in the guard bed, resulting in poor iodide removal and increased metal displacement from the metal-exchanged ion exchange resin, e.g. silver, mercury, palladium and rhodium, in the purified acetic acid. Thus, the purified acetic acid may also have unacceptable levels of iodides despite using a metal exchange guard bed. The present invention provides process for removing the lithium-containing compounds.

The source of the lithium-containing compounds may be derived from or generated by a variety of promoters, co-catalysts, additives, in situ reactions, etc. For example, low water and low energy processes that involve the use of a promoter such as lithium iodide, which may form in situ following the addition of lithium acetate or other compatible lithium salts to the reaction mixture. Therefore, process streams may contain some quantity of lithium ions derived from and/or generated by the lithium-containing compound in the reaction medium. It was previously understood that lithium ions did not affect separation and purity in the primary purification train. Thus, in one embodiment, there is provided a process for producing acetic acid comprising carbonylating at least one member selected from the group consisting of methanol, dimethyl ether, and methyl acetate in a reaction medium comprising a rhodium catalyst, water, methyl iodide and lithium-containing compounds, separating the reaction medium into a liquid recycle stream and a vapor product stream comprising acetic acid, distilling the vapor product stream in a first column to form an overhead comprising water and methyl iodide and a crude product stream comprising acetic acid, distilling the crude product stream in a second column to form a vapor sidedraw comprising acetic acid and lithium-containing compounds derived from and/or generated by the lithium-containing compound in the reaction medium, and a bottoms stream enriched in lithium-containing compounds, and feeding the vapor sidedraw, preferably a condensed portion of the vapor sidedraw, to a metal-exchanged ion exchange resin having acid cation exchange sites to produce purified acetic acid.

The lithium-containing compounds in the product stream may result from the use of organic alkali salt ligands, such as organic lithium salt ligands, such as those described CN101053841 and CN1349855, the entire contents and disclosure of which are hereby incorporated by reference. CN101053841 describes a ligand comprising lithium acetate or lithium oxalate. CN1349855 describes a bimetallic catalyst having a metal lithium organic ligand coordinating cis-dicarbonyl rhodium structure. The metal lithium organic ligand may be a pyridine derivative, such as lithium pyridine-2-formate, lithium pyridine-3-formate, lithium pyridine-4-formate, lithium pyridine-3-acetate, lithium pyridine-4-acetate, or lithium pyridine-3-propionate. In fact, the lithium salt component of all of these ligands is believed to generate lithium iodide in situ within the reaction medium after exposure to methyl iodide at reaction temperatures and pressures in the carbonylation reactor. At least some small portion of the lithium component may entrain into the purification system. Thus, the present invention may also remove lithium formed in situ from use of these types of organic ligands in the bottoms stream of the second column.

Other cations present in the second column as a result of the use of non-lithium salts, such as through the use of bimetallic Rh chelating catalysts that have an amine functionality, such as those described in CN1640543, the entire contents and disclosure of which is hereby incorporated by reference. According to CN16040543, the cation species contains N and O donor atoms and is formed from aminobenzoic acid. The amine may quaternize with methyl iodide in situ within the reaction medium at reaction temperature and pressure to form a quaternary nitrogen cation. The quaternary nitrogen cation, similar to the lithium cation, may be carried through with the crude acid product and concentration may be reduced in the vapor sidedraw.

Other Impurities in Vapor Sidedraw

In addition to lithium-containing compounds, the vapor sidedraw also comprises reduced concentrations of various others impurities. These impurities may include iodides, carbonyl-group containing impurities having a boiling point higher than acetic acid such as propionic acid, rhodium, corrosion metals such as iron, chlorides, and formic acid. In one embodiment, the process withdraws a vapor sidedraw to maintain low concentrations of these impurities. A total iodide concentration from 20 wppb to 1.5 wppm in the vapor sidedraw may be used with a metal-exchange ion exchange resin as described further herein. Thus, in one embodiment, vapor sidedraw may comprise acetic acid, lithium-containing compounds at a concentration of no more than 100 wppb, and a total iodide concentration from 20 wppb to 1.5 wppm.

The process may use 2 distillation columns in the primary purification train and preferably the primary purification does not include a column to remove heavy ends materials such as higher alkyl iodide compounds, e.g., $C_{10}$-$C_{14}$ alkyl iodides, and/or carbonyl group-containing impurities having a boiling point higher than acetic acid such as propionic acid. Without a heavy ends columns, these compounds must be removed from the second column. Preferably, these compounds are concentrated in the bottoms stream removed in the base of the second column. In one embodiment, vapor sidedraw comprises carbonyl-group containing impurities having a boiling point higher than acetic acid at a concentration that is no more than 0.1 wt. %, e.g., no more than 0.09 wt. %, no more than 0.07 wt. %, or no more than 0.05 wt. %. Thus, in one embodiment, vapor sidedraw may comprise acetic acid, lithium-containing compounds at a concentration of no more than 100 wppb, and carbonyl group-containing impurities having a boiling point higher than acetic acid at a concentration that is no more than 0.1 wt. %.

Decyl iodides and dodecyl iodides are especially prevalent in the absence of heavy ends and other finishing apparatus and are difficult to remove from the product. The vapor sidedraw in may include organic iodides with a $C_{10}$ or more aliphatic chain length which need to be removed. Sometimes more than 10% of the iodides present, e.g., more than 15%, more than 30% or even more than 50%, have an organic chain length of 10 carbon atoms or more. In one embodiment, vapor sidedraw comprises a $C_{10}$-$C_{14}$ alkyl iodide concentration of no more than 1.5 wppm, e.g., no more than 1 wppm, no more than 0.75 wppm, or no more than 0.5 wppm. Thus, in one embodiment, vapor sidedraw may comprise acetic acid, lithium-containing compounds at a concentration of no more than 100 wppb, and $C_{10}$-$C_{14}$ alkyl iodide at a concentration of no more than 1.5 wppm. These higher alkyl iodides may be in addition to the usual shorter chain length iodide impurities found in the crude acid product of an iodide-promoted carbonylation process, including methyl iodide, HI, and hexyl iodide.

Rhodium from the reaction medium may also be entrained or volatilized and fed into the second column. In one embodiment, vapor sidedraw may comprise a rhodium concentration of no more than 100 wppb as rhodium, e.g., no more than 75 wppb, no more than 50 wppb, no more than 25, no more than 20 wppb, or no more than 15 wppb. Thus, in one embodiment, vapor sidedraw may comprise acetic acid, lithium-containing compounds at a concentration of no more than 100 wppb, and a rhodium concentration of no more than 100 wppb, and a rhodium concentration of no more than 100 wppb.

The corrosion metals, such as iron, chromium, nickel and molybdenum, may also concentrate in the lower portion of second column. In one embodiment, the vapor sidedraw may comprise a total corrosion metal concentration of no more than 2 wppm, e.g., no more than 1.5 wppm, no more than 1 wppm, or no more than 0.5 wppm. In some processes, iron may be the primary corrosion metal present and the vapor sidedraw may comprise an iron concentration of no more than 1.5 wppm, e.g., no more than 1 wppm, or no more than 0.5 wppm. Thus, in one embodiment, the vapor sidedraw may comprise acetic acid, lithium-containing compounds at a concentration of no more than 100 wppb, and a total corrosion metal concentration of no more than 2 wppm.

In some embodiments, vapor sidedraw may comprise chloride in an amount of no more than 0.5 wppm, e.g., no more than 0.4 wppm, no more than 0.3 wppm, or no more than 0.2 wppm. In further embodiments, vapor sidedraw may comprise formic acid in an amount of no more than 0.01 wppm, e.g., no more than 0.009 wppm, no more than 0.008 wppm, no more than 0.007 wppm, no more than 0.006 wppm, no more than 0.005 wppm. Thus, in one embodiment, vapor sidedraw may comprise acetic acid, lithium-containing compounds at a concentration of no more than 100 wppb, chloride in an amount of no more than 0.5 wppm, and formic acid in an amount of no more than 0.01 wppm.

It should be understood that the vapor sidedraw may comprise one or more of these impurities. In an exemplary embodiment, the vapor sidedraw comprises acetic acid at a concentration of greater than or equal to 99.5 wt. %, lithium-containing compounds at a concentration of no more than 100 wppb, water at a concentration of no more than 0.2 wt. %, a total iodide concentration from 20 wppb to 1.5 wppm, carbonyl-group containing impurities having a boiling point higher than acetic acid at a concentration that is no more than 0.1 wt. %, a rhodium concentration of no more than 100 wppb as rhodium, a total corrosion metal (iron) concentration of no more than 2 wppm, chloride in an amount of no more than 0.5 wppm, and formic acid in an amount of no more than 0.01 wppm.

Other Impurities in Bottoms Stream

These impurities that may be in the vapor sidedraw may also be present in the bottoms stream. Some of the impurities may be present at elevated levels compared to the vapor sidedraw. For example, bottoms stream may comprise a total iodide concentration of no more than 50 wppm, e.g., no more than 25 wppm, or no more than 10 wppm. Bottoms stream may also comprise a concentration carbonyl-group containing impurities having a boiling point higher than acetic acid that is greater than or equal to 10 wt. %, e.g., greater than or equal to 15 wt. % or greater than or equal to 20 wt. %. In terms of ranges, the concentration carbonyl-group containing impurities having a boiling point higher than acetic acid may be from 10 to 50 wt. %, e.g., from 10 to 30 wt. %, from 10 to 25 wt. %, from 10 to 20 wt. %, or form 10 to 15 wt. %.

In one embodiment, bottoms stream may comprise a rhodium concentration of no more than 100 wppb as rhodium, e.g., no more than 75 wppb, no more than 50 wppb, no more than 25, no more than 20 wppb, or no more than 15 wppb. Bottoms stream may comprise a total corrosion metal concentration of no more than 2 wppm, e.g., no more than 1.5 wppm, no more than 1 wppm, or no more than 0.5 wppm. Bottoms stream may comprise chloride in an amount of no more than 0.5 wppm, e.g., no more than 0.4 wppm, no more than 0.3 wppm, or no more than 0.2 wppm. In further embodiments, the bottoms stream may comprise formic acid in an amount of no more than 0.01 wppm, e.g., no more than 0.009 wppm, no more than 0.008 wppm, no more than 0.007 wppm, no more than 0.006 wppm, no more than 0.005 wppm.

Acetic Acid Production Process

An exemplary acetic acid production process is described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The purification processes described herein may be useful in carbonylation processes that use methanol and/or methyl acetate, methyl formate or dimethyl ether, or mixtures thereof, to produce acetic acid in the presence of a Group VIII metal catalyst, such as rhodium, and a halogen-containing catalyst promoter. A particularly useful process is the low water rhodium-catalyzed carbonylation of methanol to acetic acid as exemplified in U.S. Pat. No. 5,001,259. Other metal catalysts, e.g., iridium-based catalysts, are contemplated as well.

Generally, the metal component, e.g., rhodium component, of the catalyst system is believed to be present in the form of a coordination compound of rhodium with a halogen component providing at least one of the ligands of such coordination compound. In addition to the coordination of rhodium and halogen, it is also believed that carbon monoxide coordinates with rhodium. The rhodium component of the catalyst system may be provided by introducing into the reaction zone rhodium in the form of rhodium metal, rhodium salts such as the oxides, acetates, iodides, carbonates, hydroxides, chlorides, etc., or other compounds that result in the formation of a coordination compound of rhodium in the reaction environment.

The metal catalyst may comprise a Group VIII metal. Suitable Group VIII catalysts include rhodium and/or iridium catalysts. When a rhodium catalyst is used, the rhodium catalyst may be added in any suitable form such that rhodium is in the catalyst solution as an equilibrium mixture including [Rh(CO)$_2$I$_2$]-anion, as is well known in the art. Iodide salts optionally maintained in the reaction mixtures of the processes described herein may be in the form of a soluble salt of an alkali metal or alkaline earth metal, quaternary ammonium, phosphonium salt or mixtures thereof. In certain embodiments, the catalyst co-promoter is lithium iodide, lithium acetate, or mixtures thereof. The salt co-promoter may be added as a non-iodide salt that generates an iodide salt. The iodide catalyst stabilizer may be introduced directly into the reaction system. Alternatively, the iodide salt may be generated in-situ since under the operating conditions of the reaction system, a wide range of non-iodide salt precursors reacts with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; 5,144,068 and 7,005,541, the entireties of which are hereby incorporated by reference. The carbonylation of methanol utilizing iridium catalyst is well known and is generally described in U.S. Pat. Nos. 5,942,460, 5,932,764, 5,883,295, 5,877,348, 5,877,347 and 5,696,284, the entireties of which are hereby incorporated by reference.

The halogen-containing catalyst promoter of the catalyst system consists of a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter may include methyl halide, and more preferably methyl iodide.

The components of the reaction medium are maintained within defined limits to ensure sufficient production of acetic acid. The reaction medium contains a concentration of the metal catalyst, e.g., rhodium catalyst, in an amount from 200 to 3000 wppm as rhodium, e.g., from 500 to 2000 wppm, or from 600 to 1500 wppm. The concentration of water in the reaction medium is maintained under low water conditions, e.g., water in amount of no more than 14 wt. %, from 0.1 wt. % to 14 wt. %, from 0.2 wt. % to 10 wt. % or most preferably from 0.25 wt. % to 5 wt. %. The concentration of methyl iodide in the reaction medium is maintained to be from 1 to 25 wt. %, e.g., from 5 to 20 wt. %, from 4 to 13.9 wt. %. The concentration of iodide salt, e.g., lithium iodide, in the reaction medium is maintained to be from 1 to 25 wt. %, e.g., from 2 to 20 wt. %, from 3 to 20 wt. %. The concentration of methyl acetate in the reaction medium is maintained to be from 0.5 to 30 wt. %, e.g., from 0.3 to 20 wt. %, from 0.6 to 4.1 wt. %. The following amounts are based on the total weight of the reaction medium. The concentration of acetic acid in the reaction medium is generally greater than or equal to 30 wt. %, e.g., greater than or equal to 40 wt. %, greater than or equal to 50 wt. %, or greater than or equal to 60 wt. %.

In one embodiment, the process for producing acetic acid further includes introducing a lithium containing-compound into the reactor to maintain the concentration of lithium acetate in an amount from 0.3 to 0.7 wt. % in the reaction medium, wherein in an exemplary embodiment, in the reaction medium the concentration of the rhodium catalyst is maintained in an amount from 200 to 3000 wppm in the reaction medium, the concentration of water is maintained in amount from 0.1 to 4.1 wt. % in the reaction medium, and the concentration of methyl acetate is maintained from 0.6 to 4.1 wt. % in the reaction medium, based on the total weight of the reaction medium present within the carbonylation reactor.

Lithium containing-compound introduced into the reactor is selected from the group consisting of lithium acetate, lithium carboxylates, lithium carbonates, lithium hydroxide, other organic lithium salts, and mixtures thereof. In one embodiment, the lithium compound is soluble in the reaction medium. In one preferred embodiment, lithium acetate dihydrate is used as the source of the lithium compound. The lithium-containing compounds in the vapor sidedraw may be the same lithium compounds that is introduced into the reactor.

Lithium acetate reacts with hydrogen iodide according to the following equilibrium reaction (I) to form lithium iodide and acetic acid:

LiOAc+HI LiI⇌HOAc  (I)

Lithium acetate is thought to provide improved control of hydrogen iodide concentration relative to other acetates, such as methyl acetate, present in the reaction medium. Without being bound by theory, lithium acetate is a conjugate base of acetic acid and thus reactive toward hydrogen iodide via an acid-base reaction. This property is thought to result in an equilibrium of the reaction (I) which favors reaction products over and above that produced by the corresponding equilibrium of methyl acetate and hydrogen iodide. This improved equilibrium is favored by water concentrations of less than 4.1 wt. % in the reaction medium. In addition, the relatively low volatility of lithium acetate compared to methyl acetate allows the lithium acetate to remain in the reaction medium except for volatility losses and small amounts of entrainment into the vapor crude product. In contrast, the relatively high volatility of methyl acetate allows the material to distill into the purification train, rendering methyl acetate more difficult to control. Lithium acetate is much easier to maintain and control in the process at consistent low concentrations of hydrogen iodide. Accordingly, a relatively small amount of lithium acetate may be employed relative to the amount of methyl acetate needed to control hydrogen iodide concentrations in the reaction medium. It has further been discovered that lithium acetate is at least three times more effective than methyl acetate in promoting methyl iodide oxidative addition to the rhodium [I] complex. However, it has been discovered that lithium cations derived from and/or generated by the lithium compound in the reaction medium may be entrained or be volatile enough to concentrate with the crude acetic acid product after purification in the primary purification trains.

In one embodiment, the concentration of lithium acetate in the reaction medium is maintained at greater than or equal to 0.3 wt. %, or greater than or equal to 0.35 wt. %, or greater than or equal to 0.4 wt. %, or greater than or equal to 0.45 wt. %, or greater than or equal to 0.5 wt. %, and/or the concentration of lithium acetate in the reaction medium is maintained at no more than 0.7 wt. %, or no more than 0.65 wt. %, or no more than 0.6 wt. %, or no more than 0.55 wt. %.

It has been discovered that an excess of lithium acetate in the reaction medium can adversely affect the other compounds in the reaction medium, leading to decrease productivity. Conversely, it has been discovered that a lithium acetate concentration in the reaction medium below about 0.3 wt. % is unable to maintain the desired hydrogen iodide concentrations in the reaction medium of below 1.3 wt. %.

In one embodiment, the lithium compound may be introduced continuously or intermittently into the reaction medium. The lithium compound may be introduced during reactor start up. In one embodiment, the lithium compound is introduced intermittently to replace entrainment losses.

Thus, in one embodiment there is provided a process for producing acetic acid comprising carbonylating at least one member selected from the group consisting of methanol, dimethyl ether, and methyl acetate in a reaction medium comprising a rhodium catalyst, water, methyl iodide and lithium acetate, wherein the concentration of lithium acetate in the reaction medium is maintained at no more than 0.7 wt. %, separating the reaction medium into a liquid recycle stream and a vapor product stream comprising acetic acid, distilling the vapor product stream in a first column to form an overhead comprising water and methyl iodide and a crude product stream comprising acetic acid, distilling the crude product stream in a second column to form a vapor sidedraw comprising acetic acid and lithium acetate at a concentration of no more than 100 wppb, and a bottoms stream enriched in lithium-containing compounds, and feeding the vapor sidedraw to a metal-exchanged ion exchange resin having acid cation exchange sites to produce purified acetic acid.

In some embodiments, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters.

The carbonylation reaction of methanol to acetic acid product may be carried out by contacting the methanol feed with gaseous carbon monoxide bubbled through an acetic acid solvent reaction medium containing the rhodium catalyst, methyl iodide promoter, methyl acetate, and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable. In the low water carbonylation process, the additional iodide ion over and above the iodide ion present as hydrogen iodide is generally present in the catalyst solution in amounts such that the total iodide ion concentration is from 1 to 25 wt. % and the methyl acetate is generally present in amounts from 0.5 to 30 wt. %, and the methyl iodide is generally present in amounts from 1 to 25 wt. %. The rhodium catalyst is generally present in amounts from 200 to 3000 wppm as rhodium.

The reaction medium may also contain impurities that should be controlled to avoid byproduct formation. One impurity in the reaction medium may be ethyl iodide, which is difficult to separate from acetic acid. Applicant has further discovered that the formation of ethyl iodide may be affected by numerous variables, including the concentration of acetaldehyde, ethyl acetate, methyl acetate and methyl iodide in the reaction medium. Additionally, ethanol content in the methanol source, hydrogen partial pressure and hydrogen content in the carbon monoxide source have been discovered to affect ethyl iodide concentration in the reaction medium and, consequently, propionic acid concentration in the final acetic acid product.

In embodiments, the propionic acid concentration in the acetic acid product may further be maintained below 250 wppm by maintaining the ethyl iodide concentration in the reaction medium at no more than 750 wppm without removing propionic acid from the acetic acid product.

In embodiments, the ethyl iodide concentration in the reaction medium and propionic acid in the acetic acid product may be present in a weight ratio from 3:1 to 1:2. In embodiments, the acetaldehyde:ethyl iodide concentration in the reaction medium is maintained at a weight ratio from 2:1 to 20:1.

In embodiments, the ethyl iodide concentration in the reaction medium may be maintained by controlling at least one of the hydrogen partial pressure, the methyl acetate concentration, the methyl iodide concentration, and/or the acetaldehyde concentration in the reaction medium.

In embodiments, the concentration of ethyl iodide in the reaction medium is maintained/controlled to be no more than 750 wppm, or e.g., no more than 650 wppm, or no more than 550 wppm, or no more than 450 wppm, or no more than 350 wppm. In embodiments, the concentration of ethyl iodide in the reaction medium is maintained/controlled at greater than or equal to 1 wppm, or e.g., 5 wppm, or 10 wppm, or 20 wppm, or 25 wppm, and no more than 650 wppm, or e.g., 550 wppm, or 450 wppm, or 350 wppm.

In embodiments, the weight ratio of ethyl iodide in the reaction medium to propionic acid in the acetic acid product may range from 3:1 to 1:2, or e.g., from 5:2 to 1:2, or from 2:1 to 1:2, or from 3:2 to 1:2.

In embodiments, the weight ratio of acetaldehyde to ethyl iodide in the reaction medium may range from 20:1 to 2:1, or e.g., from 15:1 to 2:1, from 9:1 to 2:1, or from 6:1.

Typical reaction temperatures for carbonylation may be from 150 to 250° C., e.g., 160 to 240° C., 170 to 230° C., and with the temperature range of 180 to 225° C. being a preferred range. The carbon monoxide partial pressure in the reactor can vary widely but is typically from 2 to 30 atm, e.g., from 3 to 10 atm. The hydrogen partial pressure in the reactor is typically from 0.05 to 2 atm, e.g., from 1 to 1.9 atm. In some embodiments, the process may be operated with a hydrogen partial pressure from 0.3 to 2 atm, e.g., from 0.3 to 1.5 atm, or from 0.4 to 1.5 atm. Because of the partial pressure of by-products and the vapor pressure of the contained liquids, the total reactor pressure may range from 15 to 40 atm. The production rate of acetic acid may be from 5 to 50 mol/L·h, e.g., from 10 to 40 mol/L·h, and preferably 15 to 35 mol/L·h.

Exemplary reaction and acetic acid recovery system 100 is shown in FIG. 1. As shown, methanol-containing feed stream 101 and carbon monoxide-containing feed stream 102 are directed to liquid phase carbonylation reactor 104, in which the carbonylation reaction occurs to form acetic acid.

Carbonylation reactor 104 is preferably either a stirred vessel or bubble-column type vessel, with or without an agitator, within which the reacting liquid or slurry contents are maintained, preferably automatically, a predetermined level, which preferably remains substantially constant during normal operation. Into carbonylation reactor 104, fresh methanol, carbon monoxide, and sufficient water are continuously introduced as needed to maintain suitable concentrations in the reaction medium.

In a typical carbonylation process, carbon monoxide is continuously introduced into the carbonylation reactor, desirably below the agitator, which may be used to stir the contents. The gaseous feed preferably is thoroughly dispersed through the reacting liquid by this stirring means. Gaseous purge stream 106 desirably is vented from the reactor 104 to prevent buildup of gaseous by-products and to maintain a set carbon monoxide partial pressure at a given total reactor pressure. In one embodiment, the gaseous purge stream 106 contains low amounts of hydrogen iodide of no more than 1 wt. %, e.g., no more than 0.9 wt. %, no more than 0.8 wt. %, no more than 0.7 wt. %, no more than 0.5 wt. %, no more than 0.3 wt. %. Hydrogen iodide in excess of these amounts may increase the duty on the scrubber to prevent hydrogen iodide from being purged. The temperature of the reactor may be controlled and the carbon monoxide feed is introduced at a rate sufficient to maintain the desired total reactor pressure. Stream 113 comprising a portion of the liquid reaction medium exits reactor 104.

The acetic acid production system preferably includes primary purification train 108 employed to recover the acetic acid and recycle catalyst solution, methyl iodide, methyl acetate, and other system components within the process. Primary purification train 108 include light ends column 124 and drying column 130, and the associated pumps, overhead receivers, condensers, etc. Thus, a recycled catalyst solution, such as stream 110 from flash vessel 112, and optionally one or more of recycle streams, such as streams 114, 116, 118, 120, 122, and 174, also are introduced into reactor 104. Of course, one or more of the recycle streams may be combined prior to being introduced into the reactor. The separation system also preferably controls water and acetic acid content in the carbonylation reactor, as well as throughout the system, and facilitates PRC removal.

Flash Vessel

The reaction medium is drawn off from the carbonylation reactor 104 at a rate sufficient to maintain a constant level therein and is provided to flash vessel 112 via stream 113. In flash vessel 112, the reaction medium is separated in a flash separation step to obtain a vapor product stream 122 comprising acetic acid and less volatile stream 110, e.g., a liquid recycle stream, comprising a catalyst-containing solution (predominantly acetic acid containing the rhodium and the iodide salt along with lesser quantities of methyl acetate, methyl iodide, and water), which preferably is recycled to the reactor, as discussed above. The vapor product stream 122 also comprises methyl iodide, methyl acetate, water, and permanganate reducing compounds (PRC's). Dissolved gases exiting the reactor and entering the flash vessel comprise a portion of the carbon monoxide and may also contain gaseous by-products such as methane, hydrogen, and carbon dioxide. Such dissolved gases exit the flash vessel as part of the overhead stream.

In one embodiment, vapor product stream 122 comprises acetic acid, methyl iodide, methyl acetate, water, acetaldehyde, hydrogen iodide, and lithium-containing compounds. In one embodiment, vapor product stream 122 comprises acetic acid in an amount from 45 to 75 wt. %, methyl iodide in an amount from 20 to 50 wt. %, methyl acetate in an amount of no more than 9 wt. %, and water in an amount of no more than 15 wt. %, based on the total weight of the vapor product stream. In another embodiment, vapor product stream 122 comprises acetic acid in an amount from 45 to 75 wt. %, methyl iodide in an amount from 24 to less than 36 wt. %, methyl acetate in an amount of no more than 9 wt. %, and water in an amount of no more than 15 wt. %, based on the total weight of the vapor product stream. More preferably, vapor product stream 122 comprises acetic acid in an amount from 55 to 75 wt. %, methyl iodide in an amount from 24 to 35 wt. %, methyl acetate in an amount from 0.5 to 8 wt. %, and water in an amount from 0.5 to 14 wt. %. In yet a further preferred embodiment, vapor product stream 112 comprises acetic acid in an amount from 60 to 70 wt. %, methyl iodide in an amount from 25 to 35 wt. %, methyl acetate in an amount from 0.5 to 6.5 wt. %, and water in an amount from 1 to 8 wt. %. The acetaldehyde concentration in the vapor product stream may be in an amount from 0.005 to 1 wt. %, based on the total weight of the vapor product stream, e.g., from 0.01 to 0.8 wt. %, or from 0.01 to 0.7 wt. %. In some embodiments the acetaldehyde may be present in amounts no more than 0.01 wt. %. Vapor product stream 122 may comprise hydrogen iodide in an amount of no more than 1 wt. %, based on the total weight of the vapor product stream, e.g., no more than 0.5 wt. %, or no more than 0.1 wt. %. In one embodiment, vapor product stream 122 comprises lithium-containing compounds in amounts of no more than 0.1 wt. %, e.g., no more than 0.5 wt. %, no more than 0.01, or no more than 0.0001 wt. %, based on the total weight of the vapor product stream. In some embodiments, vapor product stream 122 comprises low amounts of propionic acid, e.g., no more than 0.05 wt. %, e.g., no more than 0.01 wt. % or no more than 0.0001 wt. %, based on the total weight of the vapor product stream.

Less volatile stream 110 comprises acetic acid, the metal catalyst, corrosion metals, as well as other various compounds. In one embodiment, liquid recycle stream comprises acetic acid in an amount from 60 to 90 wt. %, metal catalyst in an amount from 0.01 to 0.5 wt. %; corrosion metals (e.g., nickel, iron and chromium) in a total amount from 10 to 2500 wppm; lithium iodide in an amount from 5 to 20 wt. %; methyl iodide in an amount from 0.5 to 5 wt. %; methyl acetate in an amount from 0.1 to 5 wt. %; water in an amount from 0.1 to 8 wt. %; acetaldehyde in an amount of no more than 1 wt. % (e.g., from 0.0001 to 1 wt. % acetaldehyde); and hydrogen iodide in an amount of no more than 0.5 wt. % (e.g., from 0.0001 to 0.5 wt. % hydrogen iodide). Although the majority of the lithium-containing compounds are withdrawn in less volatile stream 110, usually in the form of lithium iodide, other lithium-containing compounds are carried over into the vapor product stream.

Recovery of Acetic Acid

The distillation and recovery of acetic acid is not particularly limited for the purposes of the present invention. In one exemplary embodiment, there is provided a process for producing acetic acid comprising separating a reaction medium in a flash vessel to form a liquid recycle and a vapor product stream, distilling the vapor product stream in a first column, e.g., lights ends column, to obtain a crude product stream, preferably as a side stream from the first column, and a low boiling overhead vapor stream, condensing the low boiling overhead vapor stream and biphasically separating the condensed stream to form a heavy liquid phase and a light liquid phase, optionally treating a portion of the heavy liquid phase and/or the light liquid phase to remove at least one PRC, distilling the crude product stream in a second column, e.g., drying column, to form a vapor sidedraw comprising acetic acid and lithium-containing compounds at a concentration of no more than 100 wppb, and a bottoms stream enriched in lithium-containing compounds, and feeding the vapor sidedraw to a metal-exchanged ion exchange resin having acid cation exchange sites to produce purified acetic acid.

First Column

The overhead stream from flash vessel 112 is directed to the light ends column 124 as vapor product stream 122, where distillation yields a low-boiling overhead vapor stream 126, a crude product stream 128 that contains acetic acid, and a high boiling residue stream 116. As shown in FIG. 1, crude product stream 128 is removed as a side stream above the feed location of vapor product stream 122 to light ends column 124. In one embodiment, vapor product stream 122 may comprise acetic acid, methyl acetate, water, methyl iodide, and acetaldehyde, along with other impurities such as hydrogen iodide, lithium-containing compounds and crotonaldehyde, and byproducts such as propionic acid. Acetic acid removed via crude product stream 128 preferably is subjected to further purification, such as in drying column 130 for selective separation of acetic acid from water.

Light ends column 124 also preferably forms residuum or bottoms stream 116, which comprises primarily acetic acid and water. In one embodiment, bottoms stream 116 comprises lithium-containing compounds. In addition, light ends bottoms stream 116 may also comprise some residual catalyst, it may be beneficial to recycle all or a portion of light ends bottoms stream 116 to reactor 104. Optionally, light ends bottoms stream 116 may be combined with the less volatile stream 110 from flash vessel 112 and returned together to reactor 104, as shown in FIG. 1. Although the concentration of acetic acid may be relatively high in bottoms stream 116, the mass flow of the high boiling residue stream 116 relative to crude product stream 128 is very small. In one embodiment, the mass flow of the bottoms stream 116 is no more than 0.75% of crude product stream 128, e.g., no more than 0.55%, or no more than 0.45%.

In one embodiment, low-boiling overhead vapor stream 126 comprises water in amount greater than or equal to 5 wt. %, e.g., greater than or equal to 10 wt. %, or greater than or equal to 25 wt. %. The amount of water may be up to 80 wt. %. In terms of ranges, water concentration in the overhead may be from 5 wt. % to 80 wt. %, e.g., from 10 wt. % to 70 wt. % or from 25 wt. % to 60 wt. %. Reducing water concentration to less than 5 wt. % is not advantageous because this results in a large recycle of acetic acid back to the reaction system which then sets up a large recycle through the entire purification system. In addition to water, low-boiling overhead vapor stream 126 may also comprise methyl acetate, methyl iodide, and carbonyl impurities, which are preferably concentrated in the overhead to be removed from acetic acid in crude product stream 128. These carbonyl impurities may also be referred to herein as PRC's.

As shown, low-boiling overhead vapor stream 126 preferably is condensed and directed to an overhead phase separation unit, as shown by overhead decanter 134. Conditions are desirably maintained such that the condensed low-boiling overhead vapor stream 126, once in decanter 134, may separate to form a light liquid phase 138 and a heavy liquid phase 118. The phase separation should be maintain two separate phase, without forming a third phase or emulsion between the phases. An offgas component may be vented via line 136 from decanter 134. In one embodiment, the average residence time of the condensed low-boiling overhead vapor stream 126 in overhead decanter 134 is greater than or equal to 1 minute, e.g., greater than or equal to 3 minutes, greater than or equal to 5 minutes, greater than or equal to 10 minutes, and/or the average residence time is no more than 60 minutes, e.g., no more than 45 minutes, or no more than 30 minutes, or no more than 25 minutes.

Although the specific compositions of the light phase stream 138 may vary widely, some preferred compositions are provided below in Table 1.

TABLE 1

Exemplary Light Liquid Phase from Light Ends Overhead

|  | conc. (Wt. %) | conc. (Wt. %) | conc. (Wt. %) |
|---|---|---|---|
| HOAc | 1-40 | 1-25 | 5-15 |
| Water | 50-90 | 50-80 | 60-80 |
| PRC's | <5 | <3 | <1 |
| MeI | <10 | <5 | <3 |
| MeAc | 1-50 | 1-25 | 1-15 |

In one embodiment, overhead decanter 134 is arranged and constructed to maintain a low interface level to prevent an excess hold up of methyl iodide. Although the specific compositions of heavy liquid phase 118 may vary widely, some exemplary compositions are provided below in Table 2.

TABLE 2

Exemplary Heavy Liquid Phase from Light Ends Overhead

|  | conc. (Wt. %) | conc. (Wt. %) | conc. (Wt. %) |
|---|---|---|---|
| Water | 0.01-2 | 0.05-1 | 0.1-0.9 |
| Methyl Acetate | 0.1-25 | 0.5-20 | 0.7-15 |
| Acetic Acid | 0.1-10 | 0.2-8 | 0.5-6 |
| PRC's | <5 | <3 | <1 |
| Methyl Iodide | 40-98 | 50-95 | 60-85 |

The density of the heavy liquid phase 118 may be from 1.3 to 2, e.g., from 1.5 to 1.8, from 1.5 to 1.75 or from 1.55 to 1.7. As described in U.S. Pat. No. 6,677,480, the measured density in the heavy liquid phase 118 correlates with the methyl acetate concentration in the reaction medium. As density decreases, the methyl acetate concentration in the reaction medium increases. In one embodiment of the present invention, heavy liquid phase 118 is recycled to the reactor and the light liquid phase 138 is controlled to be recycled through the same pump. It may be desirable to recycle a portion of the light liquid phase 138 that does not disrupt the pump and maintains a density of the combined light liquid phase 138 and heavy liquid phase 118 of greater than or equal to 1.3, e.g., greater than or equal to 1.4, greater than or equal to 1.5, or greater than or equal to 1.7. As described herein, a portion of the heavy liquid phase 118 may be treated to remove impurities such as acetaldehyde.

As shown in FIG. 1, the light phase exits decanter 134 via stream 138. A first portion, e.g., aliquot portion, of light phase stream 138 is recycled to the top of the light ends column 124 as reflux stream 140. In other embodiments a portion of the heavy liquid phase 118 may also be refluxed (not shown) to the light ends column 124.

PRC Removal System

As described herein the light ends column 124 is part of the primary purification train. In some embodiments, a portion of light liquid phase and/or heavy liquid phase may be separated and directed to acetaldehyde or PRC removal system 132 to recover methyl iodide and methyl acetate, while removing acetaldehyde. For purposes of the present invention, the acetaldehyde or PRC removal system 132 is not part of the primary purification train.

As shown in Tables 1 and 2, light liquid phase 133 and/or heavy liquid phase 118 each contain PRC's and the process may include removing carbonyl impurities, such as acetaldehyde, that deteriorate the quality of the acetic acid product and may be removed in suitable impurity removal columns and absorbers as described in U.S. Pat. Nos. 6,143,930; 6,339,171; 7,223,883; 7,223,886; 7,855,306; 7,884,237; 8,889,904; and U.S. Pub. Nos. 2006/0011462, which are incorporated herein by reference in their entirety. Carbonyl impurities, such as acetaldehyde, may react with iodide catalyst promoters to form alkyl iodides, e.g., ethyl iodide, propyl iodide, butyl iodide, pentyl iodide, hexyl iodide, etc. Also, because many impurities originate with acetaldehyde, it is desirable to remove carbonyl impurities from the liquid light phase.

The portion of light liquid phase 138 and/or heavy liquid phase 118 fed to the acetaldehyde or PRC removal system 132 via lines 142 and 143, respectively, may vary from 1% to 99% of the mass flow of either the light liquid phase 138 and/or heavy liquid phase 118, e.g., from 1 to 50%, from 2 to 45%, from 5 to 40%, 5 to 30% or 5 to 20%. Also in some embodiments, a portion of both the light liquid phase 138 and heavy liquid phase 118 may be fed to the acetaldehyde or PRC removal system 132. The portion of the light liquid phase 138 not fed to the acetaldehyde or PRC removal system 132 may be refluxed to the first column or recycled to the reactor, as described herein. The portion of the heavy liquid phase 118 not fed to the acetaldehyde or PRC removal system 132 may be recycled to the reactor. Although a portion of heavy liquid phase 118 may be refluxed to the light ends column, it is more desirable to return the methyl iodide enriched heavy liquid phase 118 to the reactor.

In one embodiment, a portion of light liquid phase 138 and/or heavy liquid phase 118 is fed to a distillation column which enriches the overhead thereof to have acetaldehyde and methyl iodide. Depending on the configuration, there may be two separate distillation columns, and the overhead of the second column may be enriched in acetaldehyde and methyl iodide. Dimethyl ether, which may be formed in-situ, may also be present in the overhead. The overhead may be subject to one or more extraction stages to remove a raffinate enriched in methyl iodide and an extractant. A portion of the raffinate may be returned to the distillation column, first column, overhead decanter and/or reactor. For example, when the heavy liquid phase 118 is treated in the PRC removal system 132, it may be desirable to return a portion the raffinate to either the distillation column or reactor. Also, for example, when light liquid phase 138 is treated in the PRC removal system 132, it may be desirable to return a portion the raffinate to either the first column, overhead decanter, or reactor. In some embodiments, the extractant may be further distilled to remove water, which is returned to the one or more extraction stages. The column bottoms, which contains more methyl acetate and methyl iodide than light liquid phase 138, may also be recycled to reactor 104 and/or refluxed to light ends column 124.

Drying Column

Returning to the primary purification train, in addition to the overhead phase, the light ends column 124 also forms a crude product stream 128, which preferably comprises primarily acetic acid and water. Crude product stream 128 is withdrawn as a liquid side stream from light ends column 124. In order to maintain an efficient product separation, it is important that the composition of the crude product stream 128 does not vary or fluctuate significantly during normal operation. By does not vary or fluctuate significantly it is meant that the concentration of the one or more $C_1$-$C_{14}$ alkyl iodides and the concentration of methyl acetate is ±0.9% of the water concentration in the crude product stream, e.g., ±0.7%, ±0.5%, ±0.4%, ±0.3%, ±0.2%, or ±0.1%. The water concentration in the crude product stream may be from 1 to 3 wt. %, e.g., preferably from 1.1 to 2.5 wt. %. For example, when the water concentration is 2.5 wt. %, the concentration of $C_1$-$C_{14}$ alkyl iodides is from 1.6 to 3.4 wt. %, and the concentration of methyl acetate is from 1.6 to 3.4 wt. %.

Optionally, a portion of the crude product stream 128 may be recirculated to the light ends column, and in one optional embodiment, to a point below where crude product stream 128 was removed from light ends column, to improve the separation.

Since crude product stream 128 contains water in addition to acetic acid, crude product stream 128 from the light ends column 124 preferably is directed to drying column 130, in which acetic acid and water are separated from one another. As shown, drying column 130, separates crude product stream 128 to form overhead stream 144 comprised primarily of water, a vapor sidedraw 170 comprising acetic and lithium-containing compounds at a concentration of no more than 100 wppb, and a bottoms stream 174 enriched in lithium-containing compounds. Overhead stream 144 preferably is cooled and condensed in a phase separation unit, e.g., decanter 148, to form a light phase 150 and a heavy phase 122. As shown, a portion of the light phase is refluxed, as shown by stream 152 and the remainder of the light phase is returned to the reactor 104, as shown by stream 120. The heavy phase, which typically is an emulsion comprising water and methyl iodide, preferably is returned in its entirety to the reactor 104, as shown by stream 122, optionally after being combined with stream 120.

Exemplary compositions for the light phase of the drying column overhead are provided below in Table 3.

TABLE 3

Exemplary Light Phase Compositions from Drying Column Overhead

| | conc. (Wt. %) | conc. (Wt. %) | conc. (Wt. %) |
|---|---|---|---|
| HOAc | 1-20 | 1-15 | 1-10 |
| Water | 50-90 | 60-90 | 70-90 |
| MeI | <10 | <5 | <3 |
| MeAc | 1-20 | 1-15 | 1-10 |

In optional embodiments, as discussed, minor amounts of an alkali component such as KOH can be added to sidedraw 128 prior to entering the drying column 130. In other embodiments, the alkali component might also be added to the drying column 130 at the same height level as the stream 128 entering the drying column 130 or at a height above the height level height level as the stream 128 entering the drying column 130. Such addition can neutralize HI in the column.

As shown in FIG. 1, the crude acid product from the drying column 130 may be taken from a vapor sidedraw 170 at a position slightly above the bottom 172 of the column 130. In one embodiment, vapor sidedraw 170 is withdrawn within 5 trays from the bottom 172 of the column 130, e.g., within 4 trays from the bottom of the column 130, within 3 trays from the bottom of the column 130, or within 2 trays from the bottom of the column 130. In some embodiments, the vapor sidedraw 170 is withdrawn at a position between 2 and 5 trays from the bottom 172 of the column 130, e.g., a position between 3 and 5 trays from the bottom of the column 130, or position between 3 and 4 trays from the bottom of the column 130. Vapor sidedraw 170 may be withdrawn in the liquid phase so that the lithium cation would be similar to withdrawing the lithium cation concentration in the drying columns bottoms stream 146. Vapor sidedraw 170 may be advantageous over a liquid stream to reduce lithium-containing compounds in vapor sidedraw 170. When a vapor sidedraw 170 is used then other impurities such as carbonyl group-containing impurities having a boiling point higher than acetic acid, i.e. propionic acid, may advantageously concentrate in the bottoms stream 174. The compositions of vapor sidedraw 170 and bottoms stream 174 are provided above. Bottoms stream 174 may be discarded or purged from the process 100. In other embodiments, bottoms stream 174 is treated to recover acetic acid.

For purposes of the present invention, vapor sidedraw 170 may be withdrawn at a temperature above the boiling point of acetic acid at the pressure in the drying column. For example, when drying column is operated at atmospheric pressure, vapor sidedraw 170 may be withdrawn at a temperature that is greater than or equal to 118° C., e.g., greater than or equal to 120° C. or greater than or equal to 125° C. To remove iodides from vapor sidedraw 170, it may be necessary to condense the vapor sidedraw to a temperature that is suitable for the metal-exchanged ion exchange resin 184 having acid cation exchange sites. In one embodiment, vapor sidedraw 180 is passed through condenser 180 to yield a condensed sidedraw 182 that is fed to metal-exchanged ion exchange resin 184 to produce purified acetic acid 186. In one embodiment, condensed sidedraw 182 is a temperature of greater than or equal to 25° C., e.g., 35° C., or 50° C. In terms of ranges, the condensed sidedraw 182 may be a temperature within the range from 25 to 120° C., e.g., from 25 to 115° C., from 25 to 100° C., from 25 to 90° C., or from 35 to 65° C. Thus, in one embodiment, there is provided a process for producing acetic acid comprising carbonylating at least one member selected from the group consisting of methanol, dimethyl ether, and methyl acetate in a reaction medium comprising a rhodium catalyst, water, methyl iodide and lithium-containing compounds, separating the reaction medium into a liquid recycle stream and a vapor product stream comprising acetic acid, distilling the vapor product stream in a first column to form an overhead comprising water and methyl iodide and a crude product stream comprising acetic acid, distilling the crude product stream in a second column to form a vapor sidedraw comprising acetic acid and lithium-containing compounds at a concentration of no more than 100 wppb, and a bottoms stream enriched in lithium-containing compounds, condensing the vapor sidedraw to form a condensed sidedraw having a temperature from 25 to 120° C., and feeding the condensed sidedraw to a metal-exchanged ion exchange resin having acid cation exchange sites to produce purified acetic acid.

In one embodiment, vapor sidedraw 170 may be measured either on-line or off-line to determine the concentration of lithium-containing compounds. Vapor sidedraw 170 may also be measured once condensed. When the concentration of the lithium-containing compounds exceeds 100 wppb, vapor sidedraw 170 may be returned to drying column 130 for reprocessing or directed to an off-spec tank for further treatment. In other embodiments, when the measured vapor sidedraw 170 contains a concentration of the lithium-containing compounds exceed 100 wppb, the reaction conditions may be adjusted to reduce lithium acetate in the reactor. Alternatively, the conditions in drying column may be adjusted to maintain a concentration of the lithium-containing compounds of no more than 100 wppb. Thus, in one embodiment, there is provided a process for producing acetic acid comprising carbonylating at least one member selected from the group consisting of methanol, dimethyl ether, and methyl acetate in a reaction medium comprising a rhodium catalyst, water, methyl iodide and lithium-containing compounds, separating the reaction medium into a liquid recycle stream and a vapor product stream comprising acetic acid, distilling the vapor product stream in a first column to form an overhead comprising water and methyl iodide and a crude product stream comprising acetic acid, distilling the crude product stream in a second column to form a vapor sidedraw, measuring a concentration of lithium-containing compounds in vapor sidedraw, and feeding the vapor sidedraw to a metal-exchanged ion exchange resin having acid cation exchange sites to produce purified acetic acid, when the measured concentration of lithium-containing compounds is no more than 100 wppb.

Iodide Removal Beds/Use of Ion Exchange Resins

According to the present process, vapor sidedraw or condensed portions thereof, that are contaminated with halides (e.g., iodides) and have a reduced concentration of lithium-containing compounds of no more than 100 wppb may be contacted with a metal-exchanged ion exchange resin having acid cation exchange sites comprising at least one metal selected from the group consisting of silver, mercury, palladium and rhodium under a range of operating conditions. Preferably, the ion exchange resin compositions are provided in fixed beds. The use of fixed iodide removal beds to purify contaminated carboxylic acid streams is well documented in the art (see, for example, U.S. Pat. Nos. 4,615,806; 5,653,853; 5,731,252; and 6,225,498, which are hereby incorporated by reference in their entireties). Generally, a contaminated liquid carboxylic acid stream is contacted with the aforementioned ion exchange resin compositions, by flowing through a series of static fixed beds. The halide contaminants, e.g., iodide contaminants, are removed by reaction with the metal of the metal-exchanged ion exchange resin to form metal iodides. In one embodiment, the metal-exchanged ion exchange resin has a proportion of the active sites exchanged to metal from 10 to 80% by mol, e.g., from 15 to 75% by mol, from 15 to 65% by mol, from 20 to 55% by mol, or from 20 to 50% by mol. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

Similar iodide contamination issues may exist in acetic anhydride manufactured via a rhodium-iodide catalyst system. Thus, the inventive process may alternatively be utilized in the purification of crude acetic anhydride product streams.

Suitable acid-form cation exchangers for removing metal ion contaminants in the disclosed process may comprise strong acid cation exchange resins, for example strong acid macroreticular or macroporous resins, for example Amberlyst® 15 resin (DOW), Purolite C145, or Purolite CT145. The resin may also be an acid-form strong acid cation exchange mesoporous resin. Chelating resins and zeolites may also be used.

Suitably stable ion exchange resins utilized in connection with the embodiments of the present invention for preparing silver or mercury-exchanged resins for iodide removal typically are of the "RSO$_3$H" type classified as "strong acid," that is, sulfonic acid, cation exchange resins of the macroreticular (macroporous) type. Particularly suitable ion exchange substrates include Amberlyst® 15, Amberlyst® 35 and Amberlyst® 36 resins (DOW) suitable for use at elevated temperatures. Other stable ion exchange substrates such as zeolites may be employed, provided that the material is stable in the organic medium at the conditions of interest, that is, will not chemically decompose or release silver or mercury into the organic medium in unacceptable amounts. Zeolite cationic exchange substrates are disclosed, for example, in U.S. Pat. No. 5,962,735, the disclosure of which is incorporated herein by reference.

At temperatures greater than about 50° C., the silver or mercury exchanged cationic substrate may tend to release small amounts of silver or mercury on the order of 500 wppb or less and thus the silver or mercury exchanged substrate is chemically stable under the conditions of interest. More preferably, silver losses are no more than 100 wppb into the organic medium and still more preferably no more than 20 wppb into the organic medium. Silver losses may be slightly higher upon start up. In any event, if so desired a bed of acid form cationic material may be placed downstream of the silver or mercury exchange material in addition to the bed of acid form cationic material upstream of the silver or mercury exchange material, to catch any silver or mercury released.

The pressures during the contacting steps with the exchange resins are limited only by the physical strength of the resins. In one embodiment, the contacting is conducted at pressures ranging from 0.1 MPa to 1 MPa, e.g., from 0.1 MPa to 0.8 MPa or from 0.1 MPa to 0.5 MPa. For convenience, however, both pressure and temperature preferably may be established so that the contaminated carboxylic acid stream is processed as a liquid. Thus, for example, when operating at atmospheric pressure, which is generally preferred based on economic considerations, the temperature may range from 17° C. (the freezing point of acetic acid) to 118° C. (the boiling point of acetic acid). It is within the purview of those skilled in the art to determine analogous ranges for product streams comprising other carboxylic acid compounds. The temperature of the contacting step preferably is kept low enough to minimize resin degradation. In one embodiment, the contacting is conducted at a temperature ranging from 25° C. to 120° C., e.g., from 25° C. to 100° C. or from 50° C. to 100° C. Some cationic macroreticular resins typically begin significant degrading (via the mechanism of acid-catalyzed aromatic desulfonation) at temperatures of 150° C. Carboxylic acids having up to 5 carbon atoms, e.g., up to 4 carbon atoms, or up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for lithium and/or halide removal.

Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

In one embodiment, the flow rate of the vapor sidedraw, e.g., a condensed portion of the vapor sidedraw, through the resin beds ranges from 0.1 bed volumes per hour ("BV/hr") to 50 BV/hr, e.g., 3 BV/hr to 40 BV/hr, 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

A purified acetic acid composition is obtained as a result of the resin bed treatment. The purified acetic acid composition, in one embodiment, comprises iodides in an amount of no more than 100 wppb, e.g., no more than 90 wppb, no more than 50 wppb, no more than 25 wppb, or no more than 15 wppb. In one embodiment, the purified acetic acid composition comprises lithium in an amount of no more than 100 wppb, e.g., no more than 50 wppb, no more than 20 wppb, or no more than 10 wppb. In terms of ranges, the purified acetic acid composition may comprise from 0 to 100 wppb iodides, e.g., from 0 to 50 wppb, from 1 to 50 wppb, from 2 to 40 wppb; and/or from 0 to 100 wppb lithium, e.g., from 1 to 50 wppb, from 2 to 40 wppb. In other embodiments, the resin beds remove at least 25 wt. % of the iodides from the crude acetic acid product, e.g., at least 50 wt. % or at least 75 wt. %. In one embodiment, the resin beds remove at least 25 wt. % of the lithium from the crude acetic acid product, e.g., at least 50 wt. % or at least 75 wt. %.

One advantage of the embodiments of the present invention is to reduce the undesired accumulation of a metal displaced from the metal-exchanged ion exchange resin, e.g. silver, mercury, palladium and rhodium, in the purified acetic acid as the final product, when no cationic exchanger, or similar separation process, is used to removed lithium-containing compounds that may be derived from and/or generated by a lithium compound in the reaction medium. In one embodiment, the purified acetic acid comprises a metal displaced from the metal-exchanged ion exchange resin, e.g., silver, mercury, palladium and rhodium, in an amount of no more than 2000 wppb, e.g., no more than 1500 wppb, no more than 1000 wppb, no more than 500 wppb, no more than 400 wppb, no more than 300 wppb, no more than 150 wppb, no more than 100 wppb, or no more than 50 wppb. In terms of ranges, the purified acetic acid comprises a metal displaced from the metal-exchanged ion exchange resin, e.g., silver, mercury, palladium and rhodium, in an amount from 0 to 2000 wppb, e.g., from 0.1 to 1500 wppb, from 0.5 to 1000 wppb, from 1 to 500 wppb, from 1 to 400 wppb, from 1 to 300 wppb, from 1 to 150 wppb, or from 1 to 100 wppb.

Distillation

The distillation columns disclosed herein may be a conventional distillation column, e.g., a plate column, a packed column, and others. Plate columns may include a perforated plate column, bubble-cap column, Kittel tray column, uni-flux tray, or a ripple tray column. For a plate column, the theoretical number of plates is not particularly limited and depending on the species of the component to be separate, may include up to 80 plates, e.g., from 2 to 80, from 5 to 60, from 5 to 50, or more preferably from 7 to 35. The distillation column may include a combination of different distillation apparatuses. For example, a combination of bubble-cap column and perforated plate column may be used as well as a combination of perforated plate column and a packed column.

The distillation temperature and pressure in the distillation system can suitably be selected depending on the condition such as the species of the objective carboxylic acid and the species of the distillation column, or the removal target selected from the lower boiling point impurity and the higher boiling point impurity according to the composition of the feed stream. For example, in a case where the purification of acetic acid is carried out by the distillation column, the inner pressure of the distillation column (usually, the pressure of the column top) may be from 0.01 to 1 MPa, e.g., from 0.01 to 0.7 MPa, from 0.02 to 0.7 MPa, and more preferably from 0.05 to 0.5 MPa in terms of gauge pressure. Moreover, the distillation temperature for the distillation column, namely the inner temperature of the column at the temperature of the column top, can be controlled by adjusting the inner pressure of the column, and, for example, may be from 20 to 200° C., e.g., from 50 to 180° C., from 50 to 150° C. and more preferably from 100 to 160° C.

The material of each member or unit associated with the distillation system, including the columns, valves, condensers, receivers, pumps, reboilers, and internals, and various lines, each communicating to the distillation system may be made of suitable materials such as glass, metal, ceramic, or combinations thereof, and is not particularly limited to a specific one. According to the present disclosure, the material of the foregoing distillation system and various lines are a transition metal or a transition-metal-based alloy such as iron alloy, e.g., a stainless steel, nickel or nickel alloy, zirconium or zirconium alloy thereof, titanium or titanium alloy thereof, or aluminum alloy. Suitable iron-based alloys include those containing iron as a main component, e.g., a stainless steel that also comprises chromium, nickel, molybdenum and others. Suitable nickel-based alloys include those alloys containing nickel as a main component and one or more of chromium, iron, cobalt, molybdenum, tungsten, manganese, and others, e.g., HASTELLOY™ and INCONEL™. Corrosion-resistant metals may be particularly suitable as materials for the distillation system and various lines.

As is evident from the figures and text presented above, a variety of embodiments are contemplated.

E1. A process for producing acetic acid comprising: carbonylating at least one member selected from the group consisting of methanol, dimethyl ether, and methyl acetate in a reaction medium comprising a rhodium catalyst, water, methyl iodide and lithium-containing compounds comprising lithium iodide, lithium hydroxide, lithium acetate, lithium acetate dihydrate, lithium carbonate, lithium alkyl carbonate, methyllithium, lithium chloride, lithium oxalate or mixtures thereof;
separating the reaction medium into a liquid recycle stream and a vapor product stream comprising acetic acid;
distilling the vapor product stream in a first column to form an overhead comprising water and methyl iodide and a crude product stream comprising acetic acid;
distilling the crude product stream in a second column to form a vapor sidedraw comprising acetic acid and lithium-containing compounds at a concentration of no more than 100 wppb, and a bottoms stream enriched in lithium-containing compounds; and
feeding condensed portion of the vapor sidedraw to a metal-exchanged ion exchange resin having acid cation exchange sites to produce purified acetic acid.

E2. The process of embodiment E1, wherein the bottoms stream comprises lithium-containing compounds at a concentration of greater than 100 wppb.

E3. The process of anyone of embodiments E1 or E2, wherein the bottoms stream comprises lithium-containing compounds at a concentration of no more than 10 wppm.

E4. The process of anyone of embodiments E1 to E3, wherein the bottoms stream further comprises rhodium and a carbonyl group-containing impurity having a boiling point higher than acetic acid.

E5. The process of anyone of embodiments E1 to E4, wherein the bottoms stream comprises rhodium in an concentration of greater than or equal to 100 wppb.

E6. The process of anyone of embodiments E1 to E5, wherein the bottoms stream comprises the carbonyl group-containing impurity having a boiling point higher than acetic acid in an concentration of greater than or equal to 10 wt. %.

E7. The process of anyone of embodiments E1 to E6, wherein the bottoms stream further comprises acetic acid in an concentration of no more than 90 wt. %, e.g., no more than 50 wt. %.

E8. The process of anyone of embodiments E1 to E7, wherein the bottoms stream further comprises water in an concentration of no more than 0.1 wt. %.

E9. The process of anyone of embodiments E1 to E8, further comprising recovering acetic acid from the bottoms stream.

E10. The process of anyone of embodiments E1 to E9, wherein the vapor sidedraw and/or condensed sidedraw comprises the lithium-containing compounds at a concentration of no more than 50 wppb.

E11. The process of anyone of embodiments E1 to E10, wherein the vapor sidedraw and/or condensed sidedraw comprises the lithium-containing compounds at a concentration from 1 to 100 wppb.

E12. The process of anyone of embodiments E1 to E11, wherein the vapor sidedraw and/or condensed sidedraw comprises acetic acid in an concentration of greater than or equal to 99.5 wt. %.

E13. The process of anyone of embodiments E1 to E12, wherein the vapor sidedraw and/or condensed sidedraw comprises water in an concentration of no more than 0.2 wt. %.

E14. The process of anyone of embodiments E1 to E13, wherein the vapor sidedraw and/or condensed sidedraw comprises water in an concentration of no more than 0.15 wt. %.

E15. The process of anyone of embodiments E1 to E14, wherein the purified acetic acid has a displaced metal concentration of no more than 2000 wppb, wherein the displaced metals are selected from the group consisting of silver and mercury.

E16. The process of anyone of embodiments E1 to E15, wherein the purified acetic acid comprises iodides at a concentration of no more than 100 wppb.

E17. The process of anyone of embodiments E1 to E16, wherein the vapor sidedraw is withdrawn at a point within 5 actual stages from the base of the second column.

E18. The process of anyone of embodiments E1 to E17, wherein the first or the second column has an inner pressure from 0.01 to 0.7 MPa.

E19. The process of anyone of embodiments E1 to E18, wherein the temperature in the first column is about 50 to 150° C.

E20. The process of anyone of embodiments E1 to E19, wherein the metal-exchanged ion exchange resin has a proportion of the active sites exchanged to metal from 10 to 80% by mol.

E21. The process of anyone of embodiments E1 to E20, wherein the vapor sidedraw comprises iron at a concentration of no more than 1.5 wppm.

E22. The process of anyone of embodiments E1 to E21, wherein the vapor sidedraw comprises chloride at a concentration of no more than 0.5 wppm.

E23. The process of anyone of embodiments E1 to E22, wherein the vapor sidedraw comprises formic acid at a concentration of no more than 0.01 wppm.

E24. The process of anyone of embodiments E1 to E23, further comprising measuring the concentration of lithium-containing compounds in the vapor sidedraw.

E25. The process of anyone of embodiments E1 to E24, wherein the vapor sidedraw is directly fed to the metal-exchanged ion exchange resin.

E26. The process of anyone of embodiments E1 to E25, further comprising condensing the vapor sidedraw and contacting the condensed sidedraw with the metal-exchange ion exchange resin.

E27. The process of embodiment E26, wherein the condensed sidedraw has a temperature of greater than 25° C.

E28. The process of embodiment E26, wherein the rate of the condensed sidedraw to be passed through the metal exchanged ion exchange resin is about 3 to 40 bed volumes per hour.

E29. A process for producing acetic acid comprising:
carbonylating at least one member selected from the group consisting of methanol, dimethyl ether, and methyl acetate in a reaction medium comprising a rhodium catalyst, water, methyl iodide and lithium-containing compounds;

separating the reaction medium into a liquid recycle stream and a vapor product stream comprising acetic acid;

distilling the vapor product stream in a first column to form an overhead and a crude product stream comprising acetic acid;

distilling the crude product stream in a second column to form a vapor sidedraw comprising acetic acid and lithium-containing compounds at a concentration of no more than 100 wppb, and a bottoms stream enriched in lithium-containing compounds;

condensing the vapor sidedraw to form a condensed sidedraw; and feeding the condensed sidedraw to a metal-exchanged ion exchange resin having acid cation exchange sites to produce purified acetic acid.

E30. The process of embodiment E29, wherein the condensed sidedraw has a temperature of greater than 25° C.

E31. The process of embodiments E29 or E30, wherein the rate of the condensed sidedraw to be passed through the metal exchanged ion exchange resin is about 3 to 40 bed volumes per hour.

E32. The process of embodiments E29 to E31, wherein the bottoms stream comprises lithium-containing compounds at a concentration of greater than 100 wppb.

E33. The process of embodiments E29 to E32, wherein the bottoms stream comprises lithium-containing compounds at a concentration of no more than 10 wppm.

E34. The process of embodiments E29 to E33, wherein the bottoms stream further comprises rhodium and a carbonyl group-containing impurity having a boiling point higher than acetic acid.

E35. The process of embodiments E29 to E34, wherein the bottoms stream comprises rhodium in an concentration of greater than or equal to 100 wppb.

E36. The process of embodiments E29 to E35, wherein the bottoms stream comprises the carbonyl group-containing impurity having a boiling point higher than acetic acid in an concentration of greater than or equal to 10 wt. %.

E37. The process of embodiments E29 to E36, wherein the bottoms stream further comprises acetic acid in an concentration of no more than 50 wt. %.

E38. The process of embodiments E29 to E37, wherein the bottoms stream further comprises water in an concentration of no more than 0.1 wt. %.

E39. The process of embodiments E29 to E38, further comprising recovering acetic acid from the bottoms stream.

E40. The process of embodiments E29 to E39, wherein the condensed sidedraw comprises the lithium-containing compounds at a concentration of no more than 50 wppb.

E41. The process of embodiments E29 to E40, wherein the condensed sidedraw comprises the lithium-containing compounds at a concentration from 1 to 100 wppb.

E42. The process of embodiments E29 to E31, wherein the condensed sidedraw comprises acetic acid in an concentration of greater than or equal to 99.5 wt. %.

E43. The process of embodiments E29 to E42, wherein the condensed sidedraw comprises water in an concentration of no more than 0.2 wt. %.

E44. The process of embodiments E29 to E43, wherein the condensed sidedraw comprises water in an concentration of no more than 0.15 wt. %.

E45. The process of embodiments E29 to E44, wherein the purified acetic acid has a displaced metal concentration of no more than 2000 wppb, wherein the displaced metals are selected from the group consisting of silver and mercury.

E46. The process of embodiments E29 to E45, wherein the purified acetic acid comprises iodides at a concentration of no more than 100 wppb.

E47. The process of embodiments E29 to E46, wherein the vapor sidedraw is withdrawn at a point within 5 actual stages from the base of the second column.

E48. The process of embodiments E29 to E47, wherein the first or the second column has an inner pressure from 0.01 to 0.7 MPa.

E49. The process of embodiments E29 to E48, wherein the temperature in the first column is about 50 to 150° C.

E50. The process of embodiments E29 to E49, wherein the metal-exchanged ion exchange resin has a proportion of the active sites exchanged to metal from 10 to 80% by mol.

E51. The process of embodiments E29 to E50, wherein the condensed sidedraw comprises iron at a concentration of no more than 1.5 wppm.

E52. The process of embodiments E29 to E51, wherein the condensed sidedraw comprises chloride at a concentration of no more than 0.5 wppm.

E53. The process of embodiments E29 to E52, wherein the condensed sidedraw comprises formic acid at a concentration of no more than 0.01 wppm.

E54. The process of embodiments E29 to E53, further comprising measuring the concentration of lithium-containing compounds in the condensed sidedraw.

E55. The process of embodiments E29 to E54, wherein the condensed sidedraw is directly fed to the metal-exchanged ion exchange resin.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing acetic acid comprising:
    carbonylating at least one member selected from the group consisting of methanol, dimethyl ether, and methyl acetate in a reaction medium comprising a rhodium catalyst, water, methyl iodide and lithium-containing compounds;
    separating the reaction medium into a liquid recycle stream and a vapor product stream comprising acetic acid;
    distilling the vapor product stream in a first column to form an overhead and a crude product stream comprising acetic acid;
    distilling the crude product stream in a second column to form a vapor sidedraw comprising acetic acid and lithium-containing compounds at a concentration of no more than 100 wppb, and a bottoms stream enriched in lithium-containing compounds;

condensing the vapor sidedraw to form a condensed sidedraw; and feeding the condensed sidedraw to a metal-exchanged ion exchange resin having acid cation exchange sites to produce purified acetic acid.

2. The process of claim 1, wherein the lithium-containing compounds comprise lithium iodide, lithium hydroxide, lithium acetate, lithium acetate dihydrate, lithium carbonate, lithium alkyl carbonate, methyllithium, lithium chloride, lithium oxalate or mixtures thereof.

3. The process of claim 1, wherein the condensed sidedraw has a temperature of greater than 25° C.

4. The process of claim 1, wherein the bottoms stream comprises lithium-containing compounds at a concentration of greater than 100 wppb.

5. The process of claim 1, wherein the bottoms stream comprises lithium-containing compounds at a concentration of no more than 10 wppm.

6. The process of claim 1, wherein the bottoms stream further comprises a carbonyl-group containing impurity having a boiling point higher than acetic acid.

7. The process of claim 6, wherein the carbonyl-group containing impurity having a boiling point higher than acetic acid is present in an concentration of greater than or equal to 10 wt. %.

8. The process of claim 6, wherein the bottoms stream further comprises acetic acid in an concentration of no more than 50 wt. %.

9. The process of claim 6 wherein the bottoms stream further comprises water in an concentration of no more than 0.1 wt. %.

10. The process of claim 1, wherein the condensed sidedraw comprises the lithium-containing compounds at a concentration from 1 to 100 wppb.

11. The process of claim 1, wherein the condensed sidedraw comprises acetic acid in an concentration of greater than or equal to 99.5 wt. %.

12. The process of claim 1, wherein the condensed sidedraw comprises water in an concentration of no more than 0.2 wt. %.

13. The process of claim 1, wherein the purified acetic acid has a displaced metal concentration of no more than 2000 wppb, wherein the displaced metals are selected from the group consisting of silver and mercury.

14. The process of claim 1, wherein the purified acetic acid comprises iodides at a concentration of no more than 100 wppb.

15. The process of claim 1, wherein the vapor sidedraw is withdrawn at a point within 5 actual stages from the base of the second column.

16. The process of claim 1, wherein the first or the second column has an inner pressure from 0.01 to 0.7 MPa.

17. The process of claim 1, wherein the temperature in the first column is about 50 to 150° C.

18. The process of claim 1, wherein the metal-exchanged ion exchange resin has a proportion of the active sites exchanged to metal from 10 to 80% by mol.

19. The process of claim 1, wherein the condensed sidedraw comprises iron at a concentration of no more than 1.5 wppm, chloride at a concentration of no more than 0.5 wppm, and formic acid at a concentration of no more than 0.01 wppm.

20. The process of claim 1, wherein the condensed sidedraw is directly fed to the metal-exchanged ion exchange resin.

* * * * *